(12) United States Patent
Okada et al.

(10) Patent No.: US 12,370,214 B2
(45) Date of Patent: Jul. 29, 2025

(54) COMBINED PHARMACEUTICAL FORMULATION COMPRISING DRUG-CONTAINING LIPOSOME COMPOSITION AND PLATINUM PREPARATION

(71) Applicant: FUJIFILM Corporation, Tokyo (JP)

(72) Inventors: Ken Okada, Ashigarakami-gun (JP); Susumu Shimoyama, Ashigarakami-gun (JP); Mikinaga Mori, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 655 days.

(21) Appl. No.: 17/219,064

(22) Filed: Mar. 31, 2021

(65) Prior Publication Data

US 2021/0213051 A1    Jul. 15, 2021

Related U.S. Application Data

(63) Continuation of application No. PCT/JP2019/038708, filed on Oct. 1, 2019.

(30) Foreign Application Priority Data

Oct. 1, 2018 (JP) .................... 2018-186541

(51) Int. Cl.
| | |
|---|---|
| *A61K 33/243* | (2019.01) |
| *A61K 9/1271* | (2025.01) |
| *A61K 31/282* | (2006.01) |
| *A61K 31/404* | (2006.01) |
| *A61K 31/4745* | (2006.01) |
| *A61K 31/704* | (2006.01) |
| *A61P 35/00* | (2006.01) |

(52) U.S. Cl.
CPC .......... *A61K 33/243* (2019.01); *A61K 9/1271* (2013.01); *A61K 31/282* (2013.01); *A61K 31/404* (2013.01); *A61K 31/4745* (2013.01); *A61K 31/704* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,192,549 | A | 3/1993 | Barenolz et al. |
| 5,543,152 | A | 8/1996 | Webb et al. |
| 6,355,268 | B1 | 3/2002 | Slater et al. |
| 7,060,828 | B2 | 6/2006 | Madden et al. |
| 7,811,602 | B2 | 10/2010 | Cullis et al. |
| 2004/0022817 | A1* | 2/2004 | Tardi .................... A61K 9/0019 424/400 |
| 2004/0208935 | A1* | 10/2004 | Giovanella ............. A61P 35/00 600/500 |
| 2005/0129753 | A1 | 6/2005 | Gabizon et al. |
| 2006/0008909 | A1 | 1/2006 | Cullis et al. |
| 2007/0088414 | A1 | 4/2007 | Campbell et al. |
| 2007/0116753 | A1* | 5/2007 | Hong ..................... A61P 31/04 424/450 |
| 2007/0231379 | A1 | 10/2007 | Slater et al. |
| 2008/0075762 | A1 | 3/2008 | Tardi et al. |
| 2008/0206139 | A1 | 8/2008 | Connor et al. |
| 2009/0217401 | A1 | 8/2009 | Korman et al. |
| 2009/0285878 | A1 | 11/2009 | Hope et al. |
| 2011/0064794 | A1 | 3/2011 | Deng et al. |
| 2011/0159080 | A1 | 6/2011 | Lowery |
| 2011/0274625 | A1 | 11/2011 | Redelmeier et al. |
| 2012/0058178 | A1 | 3/2012 | Kikuchi et al. |
| 2013/0052259 | A1 | 2/2013 | Barenholz et al. |
| 2013/0202686 | A1 | 8/2013 | Yamashita et al. |
| 2015/0030672 | A1 | 1/2015 | Li et al. |
| 2015/0258085 | A1 | 9/2015 | Bankiewicz |
| 2016/0194625 | A1 | 7/2016 | Hoge et al. |
| 2017/0020816 | A1 | 1/2017 | Nagy et al. |
| 2017/0209574 | A1* | 7/2017 | Cao ....................... G01N 33/574 |
| 2017/0282144 | A1 | 10/2017 | Sugiyama et al. |

(Continued)

FOREIGN PATENT DOCUMENTS

| | | | |
|---|---|---|---|
| CA | 2 566 559 | * | 12/2005 |
| CA | 2 582 242 | * | 4/2006 |

(Continued)

OTHER PUBLICATIONS

Zucker et al (JCR, 160, 2012, 281-289) (Year: 2012).*
Office Action dated Jun. 27, 2023 from the Chinese Patent Office in Application No. 201880023073.9.
Office Action dated Aug. 29, 2023 from the Taiwan Patent Office in Application No. 108121444, corresponding to U.S. Appl. No. 17/125,336.
Office Action dated Mar. 25, 2023 from the Taiwan Patent Office in Application No. 108135454.
Office Action dated Mar. 9, 2023 from the Taiwanese Intellectual Property Office in TW Application No. 108121444, corresponding to U.S. Appl. No. 17/125,336.
European Office Action dated Mar. 2, 2023 in European Application No. 19823228.2, corresponding to U.S. Appl. No. 17/125,336.

(Continued)

*Primary Examiner* — Celeste A Roney
(74) *Attorney, Agent, or Firm* — Sughrue Mion, PLLC

(57) ABSTRACT

An object of the present invention is to provide a pharmaceutical formulation obtained by combining a liposome composition, in which liposomes encapsulate a drug, with a platinum preparation. According to the present invention, there is provided a pharmaceutical formulation including (A) a liposome composition in combination with (B) a platinum preparation, in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing ammonium sulfate, a molar ratio of sulfate ions in the inner water phase to the drug in an entire water phase is 0.36 or more, and the liposome composition and the platinum preparation are administered simultaneously or sequentially.

11 Claims, 2 Drawing Sheets

(56) References Cited

U.S. PATENT DOCUMENTS

| | | |
|---|---|---|
| 2018/0243214 A1 | 8/2018 | Kitahashi et al. |
| 2019/0314335 A1 | 10/2019 | Yoshino et al. |
| 2020/0016079 A1 | 1/2020 | Kasagi et al. |
| 2021/0038518 A1 | 2/2021 | Kasagi et al. |
| 2021/0100791 A1 | 4/2021 | Shimoyama et al. |
| 2022/0370352 A1 | 11/2022 | Kasagi et al. |

FOREIGN PATENT DOCUMENTS

| | | | |
|---|---|---|---|
| CN | 102764234 A | 11/2012 | |
| CN | 104771361 A | 7/2015 | |
| EP | 0 361 894 A2 | 4/1990 | |
| EP | 1 750 673 B1 | 12/2009 | |
| JP | H 02-196713 A | 8/1990 | |
| JP | 2659136 B2 | 9/1997 | |
| JP | 2006-340714 A | 12/2006 | |
| JP | 2008-519045 A | 6/2008 | |
| JP | 2016-117005 A | 6/2016 | |
| JP | 2017-512840 A | 5/2017 | |
| JP | 2020-158542 A | 10/2020 | |
| WO | WO-2005120461 A2 * | 12/2005 | ......... A61K 31/4745 |
| WO | 2006/121168 A1 | 11/2006 | |
| WO | 2010/113984 A1 | 10/2010 | |
| WO | 2012/091054 A1 | 7/2012 | |
| WO | 2013/059922 A1 | 5/2013 | |
| WO | 2017/069291 A1 | 4/2017 | |
| WO | 2017/078008 A1 | 5/2017 | |
| WO | 2017/079303 A1 | 5/2017 | |
| WO | 2018/083470 A1 | 5/2018 | |
| WO | 2018/106729 A1 | 6/2018 | |
| WO | 2018/124033 A1 | 7/2018 | |
| WO | 2018/181963 A1 | 10/2018 | |

OTHER PUBLICATIONS

Office Action dated Oct. 25, 2023 in U.S. Appl. No. 17/125,336.
Office Action dated Mar. 22, 2023 in Chinese Application No. 201980064960.5, corresponding to the present U.S. Appl. No. 17/219,064.
Office Action dated Apr. 26, 2023 in Chinese Application No. 202111595172.4, corresponding to U.S. Appl. No. 17/882,144.
Bai Xiuping et al., "Experts face to face with you on Ovarian Sugamo Cancer", China Pharmaceutical Technology Publishing Co., 2015 (4 pages total).
Jianguo Ma et al., "Synergistic cytotoxicity of cisplatin and topotecan or SN-38 in a panel of eight solid-tumor cell lines in vitro", Cancer Chemother Pharmacol, 1998, vol. 41, pp. 307-316 (10 pages total).
Leilei Xu, "Preparation and ex vivo evaluation of topotecan hydrochloride liposomes", Wanfang, 2014, pp. 27, 30, and 32-33 (7 pages total).
Michael J.W. Johnston et al., "Characterization of the drug retention and pharmacokinetic properties of liposomal nanoparticles containing dihydrosphingomyelin", Biochimica et Biophysica Acta, 2007, vol. 1768, pp. 1121-1127 (7 pages total).
Office Action dated Jan. 17, 2023 issued by the Japanese Patent Office in Japanese Application No. 2022-005193 corresponding to U.S. Appl. No. 17/882,144.
Office Action dated Jan. 6, 2023 issued by the Taiwanese Patent Office in corresponding Taiwanese Application No. 108135454.
Office Action dated Nov. 28, 2022 issued by the Chinese Patent Office in corresponding Chinese Application No. 201980064960.5.
Office Action dated Nov. 30, 2022 issued by the Chinese Patent Office in Chinese Application No. 202111595172.4 corresponding to U.S. Appl. No. 17/882,144.
Office Action issued Nov. 17, 2023 in Chinese Application No. 201880023073.9, corresponding to U.S. Appl. No. 17/882,144.
Office Action issued Mar. 11, 2024 in European Application No. 18 776 957.5, corresponding to U.S. Appl. No. 17/882,144.
Office Action dated May 13, 2024 in corresponding European Application No. 19 869 479.6.
United States Office Action issued Mar. 29, 2024 in U.S. Appl. No. 17/125,336.
Abraham et al., "An evaluation of transmembrane ion gradient-mediated encapsulation of topotecan within liposomes", Journal of Controlled Release, vol. 96, Issue 3, May 18, 2004, pp. 449-461, Abstract Only (3 pages total).
Communication dated Feb. 22, 2021, from the Korean Intellectual Property Office in application No. 10-2019-7028183.
Communication dated Feb. 26, 2021, from the Intellectual Property of India in application No. 202048031732.
Communication dated Mar. 3, 2021, from the China National Intellectual Property Administration in application No. 201880023073. 9.
Extended European Search Report dated Feb. 24, 2020 from the European Patent Office in European application No. 18776957.5.
Fritze, A. et al., "Remote loading of doxorubicin into liposomes driven by a transmembrane phosphate gradient", Biochimica et Biophysica Acta, vol. 1758, No. 10, 2006, pp. 1633-1640.
Fugit et al., "Ion-Pairing Contribution to the Liposomal Transport of Topotecan as Revealed by Mechanistic Modeling", Journal of Pharmaceutical Sciences, vol. 106, 2017, pp. 1149-1161.
Haran, G., et al., "Transmembrane ammonium sulfate gradients in liposomes produce efficient and stable entrapment of amphipathic weak bases", Biochimica et Biophysica Acta, vol. 1151, No. 2, XP023352276, 1993, pp. 201-215.
International Preliminary Report on Patentability with English Translation of Written Opinion of the International Searching Authority for PCT/JP2018/013783 dated Oct. 1, 2019, corresponding to U.S. Appl. No. 16/583,518 and U.S. Appl. No. 16/583,518.
International Preliminary Report on Patentability with English Translation of Written Opinion of the International Searching Authority for PCT/JP2019/024500 dated Dec. 22, 2020, corresponding to U.S. Appl. No. 17/125,336.
International Search Report for PCT/JP2018/013783 dated May 1, 2018 PCT/ISA/210, corresponding to U.S. Appl. No. 16/583,518 and U.S. Appl. No. 16/583,518.
International Search Report for PCT/JP2019/024500 dated Aug. 27, 2019 PCT/ISA/210, corresponding to U.S. Appl. No. 17/125,336.
M.L. Immordino et al., "Stealth liposomes: review of the basic science, rationale, and clinical applications, existing and potential", International Journal of Nanomedicine, vol. 1. No. 3, pp. 297-315, 2006 (19 pages total).
Michael Johnston et al., "Characterization of the drug retention and pharmacokinetic properties of liposomal nanoparticles containing dihydrosphingomyelin", Biochimica et Biophysica Acta 1768 (2007), pp. 1121-1127 (total 7 pages).
Noble, C., et al., "Characterization of highly stable liposomal and immunoliposomal formulations of vincristine and vinblastine", Cancer Chemotherapy and Pharmacology, 2009, vol. 64, No. 4, pp. 741-751.
Office Action dated Apr. 21, 2020, from the Russian Intellectual Property Office in Russian Application No. 2019130500/04.
Office Action dated Apr. 28, 2020, from the Australian Patent Office in Australian application No. 2018246024.
Office Action dated Mar. 19, 2020, from the Intellectual Property of India in Indian application No. 201947039515.
Office Action issued Jan. 10, 2020 in U.S. Appl. No. 16/583,518.
Office Action issued Jul. 24, 2020 in U.S. Appl. No. 16/583,518.
Silverman et al., "In vitro experiments showing enhanced release of doxorubicin from Doxil® in the presence of ammonia may explain drug release at tumor site", Nanomedicine: Nanotechnology, Biology, and Medicine, vol. 11, 2015, pp. 1841-1850 (14 pages total).
William C. Zamboni et al., "A Pharmacokinetic Study of a Novel Sphingomyelin/Cholesterol Liposomal Topotecan and Non-Liposomal Topotecan in Rats", AACR-NCI-EORTC International Conference, San Francisco, California, Oct. 22-26, 2007, #C113, total 1 page.
Written Opinion for PCT/JP2018/013783 dated May 1, 2018 PCT/ISA/237, corresponding to U.S. Appl. No. 16/583,518 and U.S. Appl. No. 16/583,518.
Written Opinion for PCT/JP2019/024500 dated Aug. 27, 2019 PCT/ISA/237, corresponding to U.S. Appl. No. 17/125,336.

(56) References Cited

OTHER PUBLICATIONS

Xu Lili, "Preparation and in vitro and in vivo evaluation of topotecan hydrochloride liposomes", Wanfang, Sep. 17, 2014 (88 pages total).
Zasadzinski, J., et al., "Novel methods of enhanced retention in and rapid, targeted release from liposomes", Current Opinion in Colloid & Interface Science, vol. 16, No. 3, 2011, pp. 203-214.
Zeghari-Squalli et al., "Cellular Pharmacology of the Combination of the DNA Topoisomerase I Inhibitor SN-38 and the Diaminocyclohexane Platinum Derivative Oxaliplatin", Clinical Cancer Research, May 1999, vol. 5, pp. 1189-1196 (9 pages total).
International Search Report for PCT/JP2019/038708 dated Dec. 10, 2019 [PCT/ISA/210].
Written Opinion of the International Searching Authority for PCT/JP2019/038708 dated Dec. 10, 2019 [PCT/ISA/237].
International Preliminary Report on Patentability with translation of Written Opinion for PCT/JP2019/038708 dated Mar. 23, 2021.
Office Action issued May 11, 2021 in U.S. Appl. No. 16/583,518.
U.S. Appl. No. 16/583,518, filed Sep. 26, 2019 (Kasagi).
U.S. Appl. No. 17/079,759, filed Oct. 26, 2020 (Kasagi).
U.S. Appl. No. 17/125,336, filed Oct. 26, 2020 (Shimoyama).
Office Action dated Sep. 20, 2024 in U.S. Appl. No. 17/125,336.
Office Action issued Sep. 24, 2021 in U.S. Appl. No. 16/583,518.
Communication issued Sep. 10, 2021 from the China National Intellectual Property Administration in Chinese Application No. 201880023073.9, corresponds to U.S. Appl. No. 16/583,518.
Notice of Reasons for Refusal issued Nov. 9, 2021 from the Japanese Patent Office in Japanese Application No. 2020-525795, corresponds to U.S. Appl. No. 16/583,518.
Extended European Search Report dated Aug. 17, 2021 in European Application No. 19869479.6.
Yasuyuki Sadzuka et al., "Effect of Polyethyleneglycol (PEG) Chain on Cell Uptake of PEG-Modified Liposomes", Journal of Liposome Research, 2003, vol. 13, No. 2, pp. 157-172 (16 pages total).
Communication dated Jun. 22, 2022 from the Chinese Patent Office in Chinese Application No. 201980064960.5.
Xu Leilei et al., "Preparation and Pharmacokinetics in Rats of Topotecan Hydrochloride Liposomes by Ammonium Sulfate Gradient Method", Chinese Journal of Pharmaceuticals, 2014, vol. 45, No. 12, pp. 1139-1142 (4 pages total).
Bowen, P., "Particle Size Distribution Measurement from Millimeters to Nanometers and from Rods to Platelets", Journal of Dispersion Science and Technology, 2002, vol. 23, No. 5, pp. 631-662 (33 pages).
Extended European Search Report issued Jul. 1, 2021 in European Application No. 19823228.2, corresponds to U.S. Appl. No. 17/125,336.
Office Action dated Jun. 23, 2021 from the Brazilian Patent Office in Application No. BR112019020406-7, corresponding to U.S. Appl. No. 16/583,518.
Non-Final Office Action issued Feb. 7, 2022 in co-pending U.S. Appl. No. 17/079,759.
Office Action dated Mar. 1, 2022 from the Japanese Patent Office in corresponding Japanese Application No. 2020-550444.
Notice of Allowance issued Mar. 16, 2022 in U.S. Appl. No. 16/583,518.
Office Action issued Apr. 26, 2022 in Chinese Application No. 201980040973.9, corresponds to U.S. Appl. No. 17/125,336.
Office Action issued Oct. 27, 2022 in Chinese Application No. 201980040973.9, corresponds to U.S. Appl. No. 17/125,336.
Notice of Allowance issued Feb. 4, 2025 in U.S. Appl. No. 17/125,336.
Office Action issued Jan. 28, 2025 in U.S. Appl. No. 17/882,144.
Leilei Xu, Preparation and in Vitro/in Vivo Evaluation of Topotecan Hydrochloride Liposomes, Master's Thesis, Jiangsu University (2014).
Office Action issued in Chinese patent application No. 202310994903.5 dated May 30, 2025, corresponding to U.S. Appl. No. 17/882,144.
Office Action issued Jun. 13, 2025, in Chinese Application No. 202310994904.X; corresponding to U.S. Appl. No. 16/583,518.

* cited by examiner

COMBINED PHARMACEUTICAL FORMULATION COMPRISING DRUG-CONTAINING LIPOSOME COMPOSITION AND PLATINUM PREPARATION

CROSS-REFERENCE TO RELATED APPLICATIONS

This application is a Continuation of PCT International Application No. PCT/JP2019/038708 filed on Oct. 1, 2019, which claims priority under 35 U.S.C § 119(a) to Japanese Patent Application No. 2018-186541 filed on Oct. 1, 2018. Each of the above application(s) is hereby expressly incorporated by reference, in its entirety, into the present application.

BACKGROUND OF THE INVENTION

1. Field of the Invention

The present invention relates to a pharmaceutical formulation in which a drug-containing liposome composition and a platinum preparation are combined and administered simultaneously or sequentially.

In chemotherapy, it is often studied that a drug is accumulated at a disease site such as cancer and exposed thereto over a long period of time by means of a liposome composition.

U.S. Pat. No. 7,060,828B2 and literature [AACR-EORTC International Conference, San Francisco, California, Oct. 22-26, 2007, #C113 A Pharmacokinetics Study of a Novel Sphingomyelin/Cholesterol Liposomal Topotecan and Non-Liposomal Topotecan in Rats, William C. Zamboni et al.] disclose a liposome in which topotecan is encapsulated in a liposome containing sphingomyelin and cholesterol. U.S. Pat. No. 7,811,602B2 discloses a liposome in which topotecan is encapsulated in a liposome containing dihydrosphingomyelin and cholesterol.

JP2008-519045A discloses a liposomal camptothecin preparation adapted to enhance the stability of camptothecin, including (a) camptothecin encapsulated in a liposome, (b) first solution which is external to the liposome and has a pH of less than or equal to 4.5, and (c) second solution which is internal to the liposome. It is also disclosed that the liposome contains dihydrosphingomyelin and cholesterol.

JP1990-196713A (JP-H02-196713A) discloses a system for effectively loading an amphiphilic drug into a liposome, including adjusting a liposome suspension in the presence of an ammonium compound or an ammonium salt, diluting the suspension with a buffering agent or a salt solution, and providing an ammonium gradient from the inside to the outside between an inner water phase and an outer water phase and a pH gradient such that the pH of the inside of the liposome is more acidic than the pH of the outside of the liposome.

U.S. Pat. No. 6,355,268B2 discloses a liposome in which topotecan is encapsulated in the presence of ammonium sulfate in a liposome containing purified hydrogenated soybean phospholipid or sphingomyelin, cholesterol, and a hydrophilic polymer derivative lipid.

Literature [Clin Cancer Res. 1999 May; 5(5): 1189-96. Cellular pharmacology of the combination of the DNA topoisomerase I inhibitor SN-38 and the diaminocyclohexane platinum derivative oxaliplatin. Nadia Zeghari-Squalli et al.] discloses that a combination of SN-38, an active metabolite of irinotecan (topoisomerase I inhibitor, CPT-11), and oxaliplatin suppressed tumor growth more than twice as much as that of oxaliplatin alone.

SUMMARY OF THE INVENTION

The above-mentioned U.S. Pat. No. 7,060,828B2, U.S. Pat. No. 7,811,602B2, JP2008-519045A, and literature [AACR-EORTC International Conference, San Francisco, California, Oct. 22-26, 2007, #C113 A Pharmacokinetics Study of a Novel Sphingomyelin/Cholesterol Liposomal Topotecan and Non-Liposomal Topotecan in Rats, William C. Zamboni et al.] disclose that the drug efficacy is improved by encapsulating topotecan or camptothecin in a liposome containing sphingomyelin or dihydrosphingomyelin to suppress the leakage of topotecan in blood and improve the area-under the blood concentration-time curve (AUC). However, since the composition of lipids that constitute the liposome and the composition of salts that precipitate topotecan have not been optimized, the improvement in AUC is not sufficient and therefore further improvement is required for AUC.

An object of the present invention is to provide a combination of two or more anticancer agents having high therapeutic effects and less side effects by combining two or more anticancer agents that act by different mechanisms, in a case where a drug-containing liposome composition is used in combination with a platinum preparation.

As a result of extensive studies, the present inventors have found that the foregoing object can be achieved by a pharmaceutical formulation including (A) a liposome composition in combination with (B) a platinum preparation, in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing ammonium sulfate, a molar ratio of sulfate ions in the inner water phase to the drug in an entire water phase is 0.36 or more, and the liposome composition and the platinum preparation are administered simultaneously or sequentially. The present invention has been completed based on these findings.

The present invention provides the following.

[1] A pharmaceutical formulation comprising:
(A) a liposome composition in combination with (B) a platinum preparation,
in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing ammonium sulfate, a molar ratio of sulfate ions in the inner water phase to the drug in an entire water phase is 0.36 or more, and the liposome composition and the platinum preparation are administered simultaneously or sequentially.

[2] The pharmaceutical formulation according to [1], in which the drug is topotecan or a salt thereof, doxorubicin or a salt thereof, irinotecan or a salt thereof, or sunitinib or a salt thereof.

[3] The pharmaceutical formulation according to [1] or [2], in which the molar ratio of the sulfate ions in the inner water phase to the drug in the entire water phase is 0.6 or more and 1.8 or less.

[4] The pharmaceutical formulation according to any one of [1] to [3], in which the hydrophilic polymer-modified diacylphosphatidylethanolamine is a polyethylene glycol- or methoxy polyethylene glycol-modified diacylphosphatidylethanolamine.

[5] The pharmaceutical formulation according to any one of [1] to [4], in which a percentage of the hydrophilic polymer-modified diacylphosphatidylethanolamine in the constitutional components of the liposome membrane is 2 to 10 mol %.

[6] The pharmaceutical formulation according to any one of [1] to [5], in which a percentage of the cholesterols in the constitutional components of the liposome membrane is 35 to 43 mol %.

[7] The pharmaceutical formulation according to any one of [1] to [6], in which a particle size is 150 nm or less.

[8] The pharmaceutical formulation according to any one of [1] to [7], in which an outer water phase has a pH of 5.5 to 8.5.

[9] The pharmaceutical formulation according to any one of [1] to [8], in which the dihydrosphingomyelin is a dihydrosphingomyelin containing a long-chain alkyl group having 16 carbon atoms and a long-chain alkyl group having 18 carbon atoms, and an included drug is topotecan or a salt thereof.

[10] The pharmaceutical formulation according to any one of [1] to [9], in which a drug release rate from a liposome in plasma having an ammonium concentration of 1 mmol/L or less is 20%/24 hours or less at 37° C., and a drug release rate from a liposome in plasma having an ammonium concentration of 4 to 6 mmol/L is 60%/24 hours or more at 37° C.

[11] The pharmaceutical formulation according to any one of [1] to [10], in which the platinum preparation includes at least one selected from carboplatin, cisplatin, oxaliplatin, or nedaplatin.

[12] The pharmaceutical formulation according to any one of [1] to [11], in which the administration is carried out at a dose and for a dosing period that exhibit a therapeutic synergistic effect.

[13] The pharmaceutical formulation according to any one of [1] to [12], in which a subject of the administration has resistance to topotecan.

[14] A method for treating a disease (preferably cancer) of a subject, comprising: simultaneously or sequentially administering (A) a liposome composition in combination with (B) a platinum preparation at an effective dose and for a dosing period in which the subject exhibits a therapeutic synergistic effect, in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing ammonium sulfate, and a molar ratio of sulfate ions in the inner water phase to the drug in an entire water phase is 0.36 or more.

[15] A pharmaceutical formulation for use in the treatment of a disease (preferably cancer) of a subject, comprising:
  (A) a liposome composition in combination with (B) a platinum preparation,
  in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing ammonium sulfate, a molar ratio of sulfate ions in the inner water phase to the drug in an entire water phase is 0.36 or more, and the liposome composition and the platinum preparation are administered simultaneously or sequentially.

[16] Use of a pharmaceutical formulation for the manufacture of medicine, the pharmaceutical formulation comprising:
  (A) a liposome composition in combination with (B) a platinum preparation,
  in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing ammonium sulfate, a molar ratio of sulfate ions in the inner water phase to the drug in an entire water phase is 0.36 or more, and the liposome composition and the platinum preparation are administered simultaneously or sequentially.

[17] A pharmaceutical formulation comprising:
  (A) a liposome composition in combination with (B) a platinum preparation,
  in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing an ammonium salt, the dihydrosphingomyelin is a dihydrosphingomyelin containing a long-chain alkyl group having 16 carbon atoms and a long-chain alkyl group having 18 carbon atoms, and the liposome composition and the platinum preparation are administered simultaneously or sequentially.

[18] A pharmaceutical formulation comprising:
  (A) a liposome composition in combination with (B) a platinum preparation,
  in which the liposome composition includes, as constitutional components of a liposome membrane, a hydrophilic polymer-modified diacylphosphatidylethanolamine; a dihydrosphingomyelin; and cholesterols, the liposome composition includes a drug, and the liposome composition and the platinum preparation are administered simultaneously or sequentially.

The pharmaceutical formulation according to an aspect of the present invention has at least one effect of treating or preventing cancer by administering a liposome composition and a platinum preparation in combination simultaneously or sequentially.

In addition, the pharmaceutical formulation according to the aspect of the present invention has a tumor growth inhibitory effect even at a low dose, which enables a desirable treatment that not only has high safety but also a low physical burden and high convenience for subjects including patients.

DESCRIPTION OF THE PREFERRED EMBODIMENTS

Figure 1:
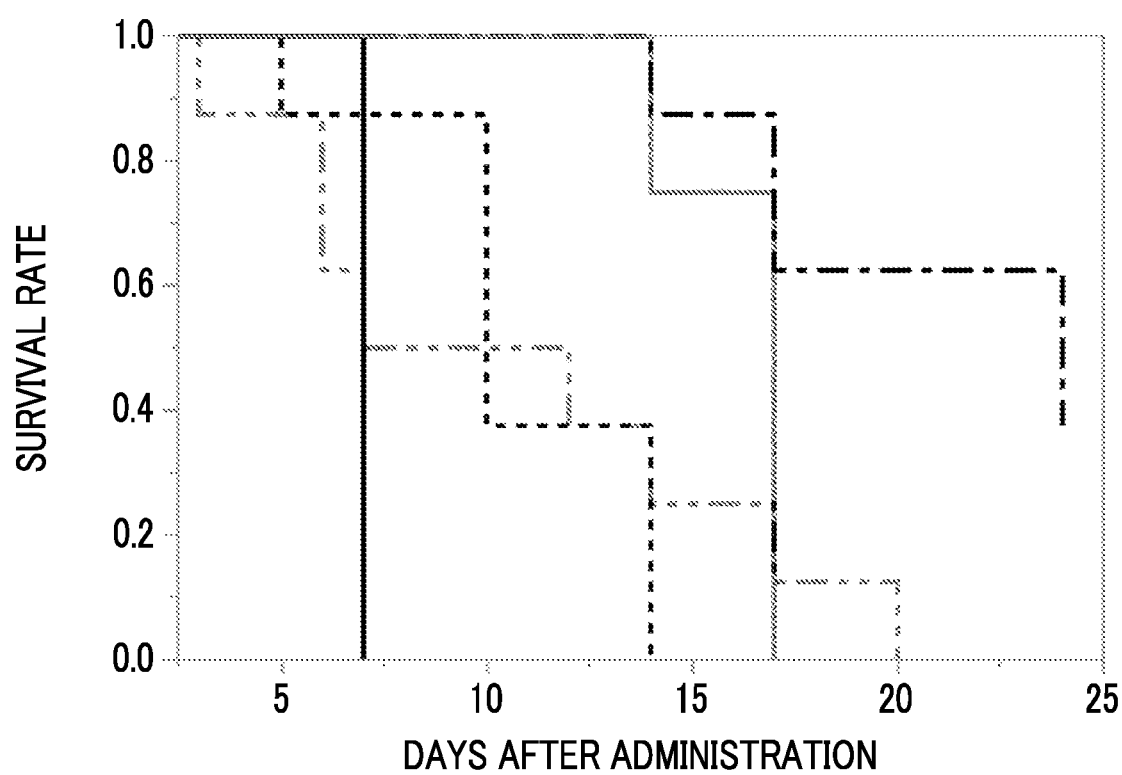
FIG. 1 shows a survival curve in a drug efficacy test using a tumor-bearing mouse model with subcutaneous transplantation of A2780.

Hereinafter, the present invention will be described in detail.

In the present specification, % means mass percentage unless otherwise specified. In the present specification, in a case where a plurality of substances corresponding to each ingredient are present in a composition, the amount of each ingredient in the composition means a total amount of the plurality of substances present in the composition, unless otherwise specified.

In the present specification, each term has the following meaning unless otherwise specified.

The term "to" indicates a range including the numerical values described before and after "to" as a minimum value and a maximum value, respectively.

The subject includes humans and mammals other than humans. Examples of mammals other than humans include monkeys, dogs, cats, cows, horses, mice, and rats.

The treatment may be any treatment or therapy that achieves a desired therapeutic effect, for example, inhibition or delay of progression of a condition, and includes slowing down a rate of progression, pausing the rate of progression, improving the condition, healing or remitting the condition (whether partial or complete), preventing, delaying, reducing, or arresting one or a plurality of symptoms and/or signs of the condition, and prolonging subject's survival over that expected in the absence of treatment.

The treatment also includes prevention. For example, treating a subject who is susceptible to or at risk of onset or recurrence of cancer may prevent or delay the onset or recurrence of cancer in the subject.

The treatment may include inhibition of cancer growth including complete remission of cancer, and/or inhibition of cancer metastasis. The cancer growth refers to the transformation of cancer into a more developed form. Examples of an index for measuring the inhibition of cancer growth include decreased survival of cancer cells, decreased tumor volume or morphology (for example, determined using computed tomography (CT), ultrasonography, or other diagnostic imaging methods), delayed tumor growth, destruction of tumor vasculature, improved scores of the delayed hypersensitivity skin test, increased activity of cytolytic T-lymphocytes, and decreased levels of tumor-specific antigens.

In the present invention, tumor, malignant tumor, cancer, malignant neoplasm, carcinoma, sarcoma, and the like are collectively referred to as "tumor" or "cancer". In addition, the term "tumor" or "cancer" includes those that have recurred after the treatment of cancer. The term "tumor" includes all malignant or benign neoplastic cell growth and proliferation, as well as pre-cancerous and cancerous cells and tissues.

The term "effective amount" is a dose required to achieve a desired therapeutic or prophylactic result, including the duration and amount of administration. The "effective amount" of the pharmaceutical formulation according to the embodiment of the present invention may vary depending on the disease state, age, sex, and body weight of a subject (or individual), the ability of the pharmaceutical formulation to elicit a desired response in the subject (or individual), and the like.

The term "co-administration" refers to administering a first therapy and a second therapy in a combination therapy at a time interval of about 15 minutes or less, such as any of about 10 minutes, about 5 minutes, about 1 minute or less. In a case where the first therapy and the second therapy are administered simultaneously, the first therapy and the second therapy can be contained in the same composition (for example, a composition that contains both the first therapy and the second therapy), or can be contained in separate compositions (for example, the first therapy is contained in one composition and the second therapy is contained in another composition).

The term "sequential administration" refers to administering a first therapy and a second therapy in a combination therapy at a time interval of more than about 15 minutes, such as any of about 20 minutes, about 30 minutes, about 40 minutes, about 50 minutes, about 60 minutes or longer (1 day, 2 days, 3 days, 1 week, 2 weeks, 3 weeks, or the like). In the present invention, the sequential administration also includes first administration of the first therapy and first administration of the second therapy. In addition, in the present invention, the sequential administration also includes the administration of the second therapy after the administration of the first therapy (after a predetermined time (for example, after 1 week)). The first therapy and the second therapy may be contained in separate compositions, which may be contained in the same package or kit or may be contained in different packages or kits.

The term "retention in blood" means a property in which a drug in a state of being encapsulated in a liposome is present in blood in a subject to which a liposome composition has been administered.

The "average particle size of liposome" means an average particle size (preferably a cumulant average particle size) measured using a dynamic light scattering method unless otherwise specified. Examples of commercially available determination devices using dynamic light scattering include a Fiber-Optics Particle Analyzer FPAR-1000 (manufactured by Otsuka Electronics Co., Ltd.), a Nanotrac UPA (manufactured by Nikkiso Co., Ltd.), and a Nanosizer (manufactured by Malvern Panalytical Ltd.). It is also possible to calculate a volume average particle size and a number average particle size of the liposome by the conversion equation specific to the determination device of each manufacturer. In order to measure particles in the vicinity of 100 nm, the distribution of particles cannot be accurately captured by a static light scattering method or the like, and measurement by the dynamic light scattering method is preferable.

(Pharmaceutical Formulation According to Embodiment of Present Invention)

Hereinafter, the present invention will be described in detail.

The first form of the pharmaceutical formulation according to the embodiment of the present invention is a pharmaceutical formulation including (A) a liposome composition in combination with (B) a platinum preparation, in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing ammonium sulfate, a molar ratio of sulfate ions in the inner water phase to the drug in an entire water phase is 0.36 or more, and the liposome composition and the platinum preparation are administered simultaneously or sequentially.

The second form of the pharmaceutical formulation according to the embodiment of the present invention is a pharmaceutical formulation including (A) a liposome composition in combination with (B) a platinum preparation, in which the liposome composition includes, as constitutional components of a liposome membrane, a hydrophilic polymer-modified diacylphosphatidylethanolamine; a dihydrosphingomyelin; and cholesterols, the liposome composition includes a drug and has an inner water phase containing an ammonium salt, the dihydrosphingomyelin is a dihydrosphingomyelin containing a long-chain alkyl group having 16 carbon atoms and a long-chain alkyl group having 18 carbon atoms, and the liposome composition and the platinum preparation are administered simultaneously or sequentially.

The third form of the pharmaceutical formulation according to the embodiment of the present invention is a pharmaceutical formulation including (A) a liposome composition in combination with (B) a platinum preparation, in which the liposome composition includes, as constitutional components of a liposome membrane, a hydrophilic polymer-modified diacylphosphatidylethanolamine; a dihydrosphingomyelin; and cholesterols, the liposome composition includes a drug, and the liposome composition and the platinum preparation are administered simultaneously or sequentially.

The following description relating to the present invention applies to the first to third forms of the pharmaceutical formulation according to the embodiment of the present invention. In addition, the present invention includes aspects resulting from modifications and/or combinations of certain forms of the present invention based on the following description relating to the present invention.

((A) Liposome Composition)

The liposome is a closed vesicular body formed of a lipid bilayer membrane using lipids, and has a water phase (inner water phase) within the space of the closed vesicle. The inner water phase contains water and the like. The liposome is usually present in a state of being dispersed in an aqueous solution (outer water phase) outside a closed vesicular body. In the present invention, the liposome composition refers to a composition including a liposome and an aqueous solution, ingredients, and the like contained outside the liposome. The liposome may be single lamellar (which is also referred to as monolayer lamellar or unilamellar, and is a structure having a single bilayer membrane) or may be multilayered lamellar (which is also referred to as multilamellar and is an onion-like structure having multiple bilayer membranes where individual layers are compartmented by aqueous layers). In the present invention, the liposome is preferably a single lamellar liposome from the viewpoint of safety and stability in pharmaceutical applications. The "encapsulating" means taking a form in which a drug is contained in an inner water phase with respect to the liposome.

The average particle size of the liposome is 10 nm to 1,000 nm, preferably 20 nm to 500 nm, more preferably 30 to 300 nm, still more preferably 30 nm to 200 nm, even more preferably 150 nm or less, for example, 30 nm to 150 nm, and particularly preferably 70 to 150 nm. The liposome preferably has a spherical shape or a shape close thereto.

In a case where an enhanced permeability and retention effect (EPR effect) is expected, the size (average particle size) of the liposome is preferably substantially 50 to 200 nm in diameter, more preferably substantially 50 to 150 nm in diameter, and still more preferably substantially 50 to 100 nm in diameter. The term "substantially" means that at least 75% of the number of liposomes are within a specified diameter range. The "at least 75%" is more preferably at least 80% and still more preferably at least 90%.

The component (membrane component) that constitutes the lipid bilayer of the liposome includes a lipid. Any lipid soluble in a mixed solvent of a water-soluble organic solvent and an ester-based organic solvent can be used as the lipid. Specific examples of the lipid include a phospholipid, a lipid other than phospholipid, cholesterols, and derivatives thereof. These components may be constituted of a single component or a plurality of components. The liposome in the present invention includes a hydrophilic polymer-modified diacylphosphatidylethanolamine, dihydrosphingomyelin, and cholesterols as the constitutional components of the liposome membrane.

Examples of the lipid serving as a base material for forming a lipid bilayer membrane include a phospholipid having two acyl chains, for example, a natural or synthetic phospholipid such as phosphatidylcholine (lecithin), phosphatidyl glycerol, phosphatidic acid, phosphatidylcholine, phosphatidyl ethanolamine, phosphatidyl serine, phosphatidyl inositol, sphingomyelin, or cardiolipin, and a hydrogenated product thereof (for example, hydrogenated soybean phosphatidylcholine (HSPC)).

In the present invention, dihydrosphingomyelin, which is a phospholipid having two acyl chains, is used as a lipid serving as a base material for forming a lipid bilayer membrane. The retention of liposomes in blood can be improved by using dihydrosphingomyelin.

By using dihydrosphingomyelin as a base material of the liposome membrane, the partition properties of the liposome membrane can be improved and therefore the leakage of the encapsulated drug can be prevented. It is speculated that this is because amide bonds of dihydrosphingomyelin have strong hydrogen bonding ability and can form a strong and highly partitionable membrane by strongly interacting with each other. In addition, amide bonds of dihydrosphingomyelin strongly interact with hydroxyl groups of cholesterol used simultaneously in the present invention, whereby a membrane having high partition properties can be formed. This is a function that cannot be achieved with commonly used lipids such as HSPC and lecithin having ester bonds.

In addition, since completely saturated dihydrosphingomyelin has a higher melting point and lower mobility of the formed membrane relative to sphingomyelin having amide bonds but having unsaturated bonds in the acyl chain, it is speculated that dihydrosphingomyelin can form a membrane with higher partition properties relative to sphingomyelin. Dihydrosphingomyelin generally has two long-chain alkyl groups in the molecule and examples of the dihydrosphingomyelin having two long-chain alkyl groups include dihydrosphingomyelin having two long-chain alkyl groups having 16 carbon atoms, dihydrosphingomyelin having a long-chain alkyl group having 16 carbon atoms and a long-chain alkyl group having 18 carbon atoms, and dihydrosphingomyelin having a long-chain alkyl group having 16 carbon atoms and a long-chain alkyl group having 20 to 24 carbon atoms.

From the viewpoint of preventing leakage of a drug from the liposome, the following compound having a long-chain alkyl group having 16 carbon atoms and a long-chain alkyl group having 18 carbon atoms is preferably used as the dihydrosphingomyelin. This is because the melting point becomes higher as the number of carbon atoms is larger, and therefore a liposome membrane having high partition properties can be formed.

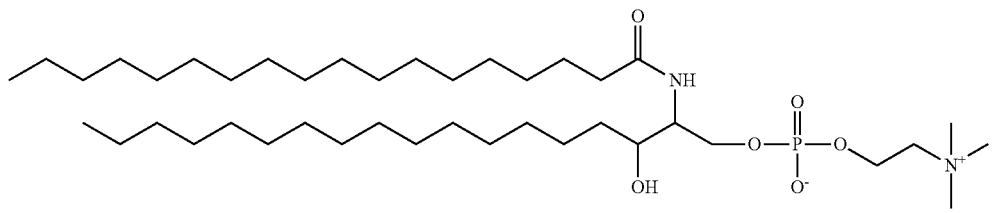 [SMILES: CCCCCCCCCCCCCCCCCC(=O)NC(COP(=O)([O-])OCC[N+](C)(C)C)C(O)CCCCCCCCCCCCCCC]

As dihydrosphingomyelin, for example, dihydrosphingomyelin obtained by reducing naturally occurring sphingomyelin by a general method may be used, or dihydrosphingomyelin obtained by synthesis may be used. Since most dihydrosphingomyelins derived from natural products such as chicken eggs generally have two long-chain alkyl groups having 16 carbon atoms, it is preferable to use dihydrosphingomyelin obtained by chemical synthesis, from the viewpoint that dihydrosphingomyelin having a long-chain alkyl group having 16 carbon atoms and a long-chain alkyl group having 18 carbon atoms can be obtained with high purity.

The percentage of dihydrosphingomyelin in the constitutional components of the liposome membrane (the total lipids constituting the liposome) is preferably 30 to 80 mol %, more preferably 40 to 70 mol %, and still more preferably 50 to 60 mol %.

Examples of the hydrophilic polymer in the hydrophilic polymer-modified diacylphosphatidylethanolamine include polyethylene glycols, polyglycerins, polypropylene glycols, polyvinyl alcohols, styrene-maleic acid anhydride alternating copolymers, polyvinylpyrrolidones, and synthetic polyamino acids. The hydrophilic polymers may be used alone or in a combination of two or more thereof.

Among these, from the viewpoint of retention in blood of a composition, polyethylene glycols, polyglycerins, and polypropylene glycols are preferable, and polyethylene glycol (PEG), polyglycerin (PG), polypropylene glycol (PPG), and derivatives thereof are more preferable.

Polyethylene glycol (PEG) and derivatives thereof are still more preferable from the viewpoint of versatility and retention in blood. Examples of derivatives of polyethylene glycol (PEG) include, but are not particularly limited to, methoxy polyethylene glycols.

The molecular weight of polyethylene glycols is not particularly limited and is 500 to 10,000 daltons, preferably 1,000 to 7,000 daltons, and more preferably 2,000 to 5,000 daltons.

The number of carbon atoms in the acyl moiety of diacylphosphatidylethanolamine is preferably 16 or more, for example, preferably 16 or more and 30 or less, more preferably 16 or more and 24 or less, and still more preferably 20.

Examples of the polyethylene glycol-modified diacylphosphatidylethanolamine include 1,2-distearoyl-3-phosphatidylethanolamine-polyethylene glycols such as 1,2-distearoyl-3-phosphatidylethanolamine-PEG2000 (manufactured by NOF Corporation), 1,2-distearoyl-3-phosphatidylethanolamine-PEG5000 (manufactured by NOF Corporation), and distearoyl glycerol-PEG2000 (manufactured by NOF Corporation).

The percentage of the hydrophilic polymer-modified diacylphosphatidylethanolamine in the constitutional components of the liposome membrane (the total lipids constituting the liposome) is preferably 1 to 15 mol % and more preferably 2 to 10 mol %.

Examples of cholesterols include cholesterols with cyclopentahydrophenanthrene as a basic skeleton in which carbon atoms thereof are partially or completely hydrogenated and derivatives thereof. For example, cholesterol is preferable. In a case where the average particle size of the liposome decreases to 100 nm or less, the curvature of the lipid membrane may become higher. The deformation of the membrane arranged in the liposome also becomes larger. It is effective to add cholesterol or the like in order to fill the deformation of the membrane caused by lipid (membrane-stabilizing effect).

In connection with the liposome, the addition of cholesterol is expected to lower the fluidity of the membrane of the liposome, for example, by filling the gaps in the membrane of the liposome.

The percentage of cholesterol in the constitutional components of the liposome membrane (lipids constituting the liposome) is preferably 20 mol % to 50 mol %, more preferably 30 mol % to 45 mol %, and still more preferably 35 mol % to 43 mol %.

In addition to the foregoing ingredients, a hydrophilic polymer or the like for improving retention in blood, fatty acid, diacetyl phosphate, or the like as a membrane structure stabilizer, or α-tocopherol or the like as an antioxidant may be added to the liposome. In the present invention, it is preferable not to include an additive such as a dispersion aid which is not approved for use in intravenous injection in pharmaceutical applications, for example, a surfactant.

(Drug)

The liposome composition includes a liposome containing a drug (hereinafter, also referred to as the liposome composition according to the embodiment of the present invention). The liposome composition according to the embodiment of the present invention includes a pharmaceutically acceptable additive, a solvent, and the like, if necessary.

The type of drug is not particularly limited, but anticancer agents given below can be used.

Specific examples of the drug include anthracycline-based anticancer agents such as doxorubicin, daunorubicin, and epirubicin;

cisplatin-based anticancer agents such as cisplatin and oxaliplatin;

taxane-based anticancer agents such as paclitaxel and docetaxel;

vinca alkaloid-based anticancer agents such as vincristine and vinblastine;

bleomycin-based anticancer agents such as bleomycin;

sirolimus-based anticancer agents such as sirolimus;

camptothecin-based anticancer agents such as topotecan (also referred to as nogitecan), irinotecan, Karenitecin (registered trademark) (also referred to as BNP1350), exatecan, lurtotecan, gimatecan (also referred to as ST1481), and belotecan (also referred to as CKD602);

vinca alkaloid-based anticancer agents such as vincristine; and molecularly targeted drugs such as imatinib (Gleevec (registered trademark)), everolimus (Afinitor (registered trademark)), erlotinib (Tarceva (registered trademark)), gefitinib (Iressa (registered trademark)), sunitinib (Sutent (registered trademark)), sorafenib (Nexavar (registered trademark)), dasatinib (Sprycel (registered trademark)), tamibarotene (Amnolake (registered trademark)), tretinoin (Vesanoid (registered trademark)), bortezomib (Velcade (registered trademark)), and lapatinib (Tykerb (registered trademark)).

Among the foregoing drugs, topotecan (including nogitecan), doxorubicin, irinotecan, or sunitinib is preferable, and topotecan is more preferable.

Nogitecan hydrochloride (generic name, chemical name: (+)-(4S)-10-[(dimethylamino)methyl]-4-ethyl-4,9-dihydroxy-1H-pyrano[3',4':6,7]indolizino[1, 2-b]quinoline-3,14 (4H,12H)-dione monohydrochloride) is preferably applicable as the topotecan, and is commercially available, for example, under a trade name of HYCAMTIN (registered trademark).

The drug may be used in the form of a salt.

Examples of the salt of the drug include salts of a basic group such as an amino group, and an acidic group such as a hydroxyl group or a carboxyl group, which are commonly known in the related art.

Examples of the salt of a basic group include salts with mineral acids such as hydrochloric acid, hydrobromic acid, phosphoric acid, boric acid, nitric acid, and sulfuric acid; salts with organic carboxylic acids such as formic acid, acetic acid, lactic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of the salt of an acidic group include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

The content of the drug in the liposome composition is not particularly limited, but is preferably 0.025 to 20 mg/ml and more preferably 0.25 to 10 mg/ml with respect to the liposome composition.

The amount of liposome-encapsulated drug relative to the liposome membrane-forming lipid is preferably 0.1 to 1.5 and more preferably 0.2 to 0.3 in terms of molar ratio from the viewpoint of the release rate of the drug from the liposome, the osmotic pressure inside the liposome, and the liposome shape by the precipitated drug.

In a case where the molar ratio of the amount of drug to the lipid is too low, the area of the liposome membrane with respect to the unit drug amount is increased, the release rate of the drug from the liposome is increased, and therefore the function of improving the retention in blood is impaired. On the other hand, in a case where the molar ratio of the amount of drug to lipid is too high, the osmotic pressure inside the liposome is increased with an increased amount of the drug dissolved, thus resulting in destruction of the liposome, or in a case where the drug is precipitated inside the liposome, the precipitated solid grows large, thus resulting in deformation of the liposome shape.

(Ammonium Sulfate in Inner Water Phase)

The inner water phase of the liposome in the present invention contains ammonium sulfate. In addition, in the liposome composition which is the first embodiment of the present invention, the molar ratio of sulfate ions in the inner water phase to the drug in the entire water phase is 0.36 or more and preferably 0.4 or more. The molar ratio of sulfate ions in the inner water phase to the drug in the entire water phase is more preferably 0.4 or more and 1.8 or less and still more preferably 0.6 or more and 1.8 or less. By setting the molar ratio of sulfate ions in the inner water phase to the drug in the entire water phase as described above, it is possible to suppress leakage of the drug from the liposome in blood.

In a case where the molar ratio of sulfate ions in the inner water phase to the drug in the entire water phase is too low, this leads to incomplete formation of a solid of the drug due to the sulfate, an increased concentration of the drug in a dissolved state, which results in increased permeability of the liposome membrane in the liposome, and easy leakage of the drug from the liposome, so that the effect of improving retention in blood is impaired. In addition, in a case where the molar ratio of sulfate ions in the inner water phase to the drug in the entire water phase is too high, the osmotic pressure inside the liposome is increased, resulting in the destruction of the liposome structure, so the drug is likely to leak out of the liposome and therefore the effect of improving retention in blood is impaired.

In addition, in the present invention, the percentage of sulfate ions contained in the inner water phase of the liposome to sulfate ions in the entire liposome composition (ratio of sulfate ions in inner water phase) is preferably at least 80% and more preferably 90% or more, and simultaneously the percentage of the drug contained in the inner water phase of the liposome to the drug in the entire liposome composition (ratio of the drug in the inner water phase) is preferably at least 80% and more preferably 90% or more.

The drug concentration in the liposome can be measured, for example, by liquid chromatography/UV-vis absorbance detection. In addition, the sulfate ion concentration in the inner water phase of the liposome can be measured, for example, by ion chromatography.

(pH of Outer Water Phase)

The liposome composition according to the embodiment of the present invention can include a liposome encapsulating a drug, and an aqueous solvent (outer water phase) in which the liposome is dispersed. The outer water phase preferably has a neutral pH and specifically a pH of about 5.5 to 8.5.

In a case where drug leakage is extremely suppressed, drug leakage at the affected site, particularly at the tumor site, may also be suppressed, and therefore the expected drug efficacy may not be obtained.

The liposome composition according to the embodiment of the present invention has a surprising mechanism of suppressing drug leakage in blood, delivering a sufficient amount of drug to the tumor site, and rapidly releasing the drug in the tumor site.

The tumor site has a property that an ammonium concentration is higher than that in other organs such as blood (see, for example, Nanomedicine: Nanotechnology, Biology, and Medicine, 11(2015) 1841-1850), and therefore the liposome composition according to the embodiment of the present invention may exhibit significantly increased drug release in an environment in which glutamine metabolism is enhanced and therefore an ammonium concentration is high (5 mmol/L), such as a tumor.

The liposome composition according to the embodiment of the present invention has a drug release rate of 20%/24 hours or less at 37° C. from liposomes in plasma having an ammonium concentration of 1 mmol/L or less and a drug release rate of 60% or more from liposomes in plasma having an ammonium concentration of 4 to 6 mmol/L; and more preferably a drug release rate of 15%/24 hours or less at 37° C. from liposomes in plasma having an ammonium concentration of 1 mmol/L or less and a drug release rate of 70% or more from liposomes in plasma having an ammonium concentration of 4 to 6 mmol/L.

(Method for Producing Liposome Composition)

The method for producing the liposome composition according to the embodiment of the present invention is not particularly limited.

For example, the liposome composition according to the embodiment of the present invention can be produced by the following steps:

(a) preparation of an oil phase;
(b) preparation of a water phase;
(c) formation of liposome particles by emulsification;
(d) particle size regulation by an extruder;
(e) replacement of liposome outer water phase liquid by dialysis;
(f) encapsulation of drug in liposome particles by remote loading; and
(g) removal of outer water phase drug by dialysis. The particle size regulation by an extruder (d) may or may not be carried out.

<(a) Preparation of Oil Phase>

(a) In the preparation of an oil phase, individual components (hydrophilic polymer-modified diacylphosphatidylethanolamine, dihydrosphingomyelin, and cholesterols) constituting the liposome and an organic solvent are mixed, and the mixture is heated to dissolve the components, whereby the oil phase can be produced.

Although the organic solvent used in the oil phase is not particularly limited, for example, a water-soluble organic solvent which is optionally mixed with water can be used.

Examples of the water-soluble organic solvent include alcohols such as methanol, ethanol, n-propanol, isopropanol, n-butanol, isobutanol, and t-butanol; glycols such as glycerin, ethylene glycol, and propylene glycol; and polyalkylene glycols such as polyethylene glycol. Among these, alcohols are preferred. The alcohol is preferably at least one selected from ethanol, methanol, 2-propanol, or t-butanol, more preferably at least one selected from ethanol, 2-propanol, or t-butanol, and still more preferably ethanol.

The concentration of each component constituting the liposome is not particularly limited and can be appropriately adjusted.

<(b) Preparation of Water Phase>

Water (distilled water, water for injection, or the like), physiological saline, various buffer solutions or aqueous solutions of sugars (sucrose or the like), or mixtures thereof (aqueous solvent) can be used as the water phase. In the present invention, it is preferable to use an aqueous ammonium sulfate solution as the water phase, in a case where a drug is encapsulated in liposome particles by remote loading which will be described later.

The buffer solution is not limited to organic and inorganic buffer solutions, and a buffer solution having a buffering action in the vicinity of a hydrogen ion concentration close to that of the body fluid is suitably used and examples thereof include a phosphate buffer solution, a Tris buffer solution, a citrate buffer solution, an acetate buffer solution, and a Good's buffer solution. The inner water phase of the liposome may be an aqueous solution in which the liposomes are dispersed in a case of producing liposomes, or may be water, physiological saline, various buffer solutions, aqueous solutions of sugars, or a mixture thereof which is newly added. The water used as an outer water phase or an inner water phase is preferably free from impurities (dust, chemicals, or the like).

The physiological saline refers to an inorganic salt solution adjusted to be isotonic with the human body fluid, and may further have a buffering function. Examples of the physiological saline include saline containing 0.9 w/v % (mass/volume percent) of sodium chloride, PBS, and Tris buffered physiological saline.

In the present invention, the water phase includes both an outer water phase and an inner water phase.

The outer water phase in the present invention means an aqueous solution in which liposomes are dispersed. For example, in a case of an injection, a solution occupying the outside of the liposome of a dispersion liquid of liposomes packaged and stored in a vial or prefilled syringe becomes an outer water phase. In addition, similarly for a liquid to be dispersed at the time of use in a case of being administered by means of an attached liquid for dispersion or other dissolution liquid, a solution occupying the outside of the liposome of a dispersion liquid of liposomes becomes an outer water phase.

The inner water phase in the present invention refers to a water phase in the closed vesicle separated by the lipid bilayer membrane of the liposome.

<(c) Formation of Liposome Particles by Emulsification>

In the emulsifying step, an oil phase and a water phase are mixed to prepare an aqueous solution containing lipids, which can be then emulsified with stirring. An oil phase where lipid has been dissolved in an organic solvent and a water phase are mixed, stirred, and emulsified to thereby prepare an emulsion where the oil phase and the water phase are emulsified in an oil-in-water type (O/W type). After mixing, liposomes are formed by removing a portion or all of the organic solvent derived from the oil phase by evaporation. Alternatively, a portion or all of the organic solvent in the oil phase is evaporated in the course of the stirring-emulsification to form liposomes.

As a method of stirring, ultrasonic waves or mechanical shearing force is used for particle miniaturization. In addition, extruder processing of allowing to pass through a filter having a certain pore size or microfluidizer processing can be carried out for uniformity of particle sizes. Use of an extruder or the like can result in decomposition of secondarily formed multivesicular liposomes into univesicular liposomes.

The emulsifying step is not limited as long as it is a step of emulsification, but it is preferably a step of applying a high shearing force and performing microparticulation with an emulsifying step including an organic solvent. The high shear rate is defined in terms of circumferential speed of a stirring blade of an emulsification machine and is preferably 5 m/s to 32 m/s and particularly preferably 20 m/s to 30 m/s. If necessary, evaporation (desolvation) of the organic solvent used in the emulsifying step may be carried out to form liposomes.

The liquid temperature in the emulsifying step in a case of producing liposomes can be appropriately adjusted, but the liquid temperature at the time of mixing an oil phase and a water phase is preferably equal to or higher than a phase transition temperature of the lipid to be used. For example, in a case where a lipid having a phase transition temperature of 35° C. to 40° C. is used, the liquid temperature at the time of mixing an oil phase and a water phase is preferably 35° C. to 70° C.

In the emulsifying step, the organic solvent and water may be evaporated from the aqueous solution containing the liposomes. As to the evaporation referred to herein, a portion or all of the organic solvent derived from the oil phase and the water derived from the water phase may be evaporated and forcibly removed, or a portion or all of the organic solvent derived from the oil phase and the water derived from the water phase may evaporate naturally in the course of stirring-emulsification.

The method of evaporation is not particularly limited, and for example, at least one of a step of heating to evaporate an organic solvent and water, a step of continuing the standing or slow stirring after emulsification, or a step of carrying out vacuum degassing may be carried out.

<(d) Particle Size Regulation by Extruder>

The obtained liposomes can be made uniform in particle size by using dialysis, filtration, extrusion processing, or the like.

The extrusion processing means a step of passing liposomes through a filter having a fine pore to apply a physical shearing force, thereby carrying out microparticulation of the liposomes. In a case where the liposomes are passed through, rapid microparticulation thereof may be achieved by incubating the liposome dispersion liquid and the filter at a temperature higher than or equal to the phase transition temperature of the membrane constituting the liposome.

In addition, the particle size regulation by an extruder may or may not be carried out.

<(e) Replacement of Liposome Outer Water Phase Liquid by Dialysis>

In the present invention, in a case where the drug is encapsulated in the liposome particles by remote loading, the liposome outer water phase liquid may be replaced by dialysis. An aqueous solution of 0.05% to 5% by mass of NaCl can be used as a dialysis liquid which is not particularly limited. Dialysis of the liposome liquid using the above-mentioned dialysis liquid can provide liposomes in which ammonium sulfate present in the outer water phase is removed and the outer water phase is replaced with the dialysis liquid.

<(f) Encapsulation of Drug in Liposome Particles by Remote Loading Method>

In the present invention, it is preferable to encapsulate a drug in liposome particles by a remote loading method.

In the present invention, the remote loading method refers to a method of producing an empty liposome in which a drug is not encapsulated and then adding the drug to the liposome outer liquid to introduce the drug into the liposome. The method of remote loading is not particularly limited, but a method using an ammonium salt is preferable and a method using ammonium sulfate is more preferable.

In the remote loading method, the drug added to the outer liquid is actively transferred to liposomes and incorporated into the liposomes. A solubility gradient, an ion gradient, a pH gradient, or the like is used as the driving force. For example, there is a method of introducing a drug into liposomes using an ion gradient formed across a liposome membrane. For example, there is a technique of adding a drug into liposomes that are preformed by the remote loading method using a $Na^+/K^+$ concentration gradient.

Among the ion gradients, a proton concentration gradient is commonly used. For example, there is an aspect in which the inner (inner water phase) pH of the liposome membrane has a pH gradient lower than the outer (outer water phase) pH. The pH gradient can be specifically formed by a concentration gradient of ammonium ion gradient or the like.

<(g) Removal of Outer Water Phase Drug by Dialysis>

The drug-encapsulated liposome liquid may be subjected to dialysis to remove the drug not contained in the liposomes. For example, by subjecting the drug-encapsulated liposome liquid to dialysis, using a predetermined concentration of sucrose/histidine buffer solution as a dialysis liquid, the drug present in the outer water phase can be removed to obtain a liposome composition in which the outer water phase is replaced with the dialysis liquid.

<Sterile Filtration>

The liposome composition obtained above is preferably subjected to sterile filtration. Regarding the filtration method, it is possible to remove unwanted materials from an aqueous solution containing liposomes by using a hollow fiber membrane, a reverse osmosis membrane, a membrane filter, or the like. In the present invention, it is preferable to filter the liposome composition through a filter having a sterilizable pore size (preferably a 0.2 μm filtration sterilization filter).

To prevent an effect of deformation of liposomes on the average particle size, the sterile filtration step and the below-described aseptic filling step are preferably carried out at a temperature lower than or equal to the phase transition temperature of the lipid constituting the liposome. For example, in a case where the phase transition temperature of the lipid is around 50° C., the sterile filtration step and the below-described aseptic filling step are carried out at temperature of preferably about 0° C. to 40° C., and more specifically about 5° C. to 30° C.

<Aseptic Filling>

The liposome composition obtained after sterile filtration is preferably aseptically filled for medical applications. Known methods can be applied for aseptic filling. A liposome composition suitable for medical applications can be prepared by aseptically filling the liposome composition in a container.

(Liposome Composition)

In connection with the route of administration, the liposome composition according to the embodiment of the present invention may also contain at least one of a tonicity agent, a stabilizer, an antioxidant, or a pH adjusting agent which is pharmaceutically acceptable. That is, the liposome composition according to the embodiment of the present invention can be provided as a pharmaceutical composition.

The tonicity agent is not particularly limited and examples thereof include inorganic salts such as sodium chloride, potassium chloride, sodium hydrogen phosphate, sodium dihydrogen phosphate, and potassium dihydrogen phosphate; polyols such as glycerol, mannitol, and sorbitol; and sugars such as glucose, fructose, lactose, and sucrose.

The stabilizer is not particularly limited and examples thereof include sugars such as glycerol, mannitol, sorbitol, lactose, and sucrose.

The antioxidant is not particularly limited and examples thereof include ascorbic acid, uric acid, tocopherol homologues (for example, vitamin E, four tocopherol isomers α, β, γ, and δ), cysteine, and ethylenediaminetetraacetic acid (EDTA). Stabilizers and antioxidants may be respectively used alone or in a combination of two or more thereof.

Examples of the pH adjusting agent include sodium hydroxide, citric acid, acetic acid, triethanolamine, sodium hydrogen phosphate, sodium dihydrogen phosphate, and potassium dihydrogen phosphate.

The liposome composition according to the embodiment of the present invention may contain a pharmaceutically acceptable organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerin, propylene glycol, polyethylene glycol, vaseline, paraffin, stearyl alcohol, stearic acid, human serum albumin (HSA), mannitol, sorbitol, lactose, phosphate buffered saline (PBS), sodium chloride, sugars, a biodegradable polymer, a serum-free medium, or an additive which is acceptable as a pharmaceutical additive.

The container in which the liposome composition according to the embodiment of the present invention is filled is not particularly limited, and it is preferably made out of a material having low oxygen permeability. Examples of the container include a plastic container, a glass container, and a laminated film bag with an aluminum foil, an aluminum vapor deposition film, an aluminum oxide vapor deposition film, a silicon oxide vapor deposition film, a polyvinyl alcohol, an ethylene-vinyl alcohol copolymer, a polyethylene terephthalate, a polyethylene naphthalate, a polyvinylidene chloride, or the like as a gas barrier layer. The container can be shielded from light by employing, for example, a bag using colored glass, an aluminum foil, an aluminum vapor deposition film, or the like, if necessary.

In the container in which the liposome composition is filled, in order to prevent oxidation due to oxygen existing in the space inside the container, it is preferable to replace the gas in the container space and drug solution with an inert gas such as nitrogen. For example, an injection solution is bubbled with nitrogen, and then the filling of the injection solution into a container can be carried out under a nitrogen atmosphere.

The administration route of the liposome composition according to the embodiment of the present invention is preferably parenteral administration. Examples of the parenteral administration include intravenous injection such as intravenous drip, intramuscular injection, intraperitoneal injection, subcutaneous injection, intraocular injection, and intrathecal injection. The administration method of the liposome composition may be, for example, administration by syringe or intravenous drip.

The dosage and frequency of administration of the liposome composition according to the embodiment of the present invention may be appropriately set depending on the type of drug, the condition of the patient, and the like. The dose of the liposome composition can be generally set in a range of 0.01 mg/kg/day to 100 mg/kg/day in terms of the mass of drug which is an active ingredient. The dose of the liposome composition can be set in a range of 2 mg to 10 mg per administration in terms of the mass of drug which is an active ingredient. The dose of the liposome composition according to the embodiment of the present invention is not limited to these dosages.

((B) Platinum Preparation)

In the present invention, a platinum preparation is used as a medicine to be administered simultaneously or sequentially in combination with the drug-containing liposome composition according to the embodiment of the present invention. The platinum preparation means a preparation containing a compound containing platinum as an active ingredient, which has an anticancer effect. The platinum preparation may contain a pharmaceutically acceptable additive, a solvent, and the like in addition to the compound containing platinum as an active ingredient.

Preferred platinum preparations in the present invention include carboplatin, cisplatin, oxaliplatin, nedaplatin, and miriplatin. In the present invention, one or a plurality of platinum preparations can be used. The platinum preparation can be obtained by purchasing commercially available products thereof. Examples of preferred platinum preparations in the present invention include carboplatin, cisplatin, oxaliplatin, and nedaplatin.

Further, the platinum preparation will be described. Cisplatin (CAS: 15663-27-1) is presumed to be effective in cancer types such as testicle tumor, bladder cancer, prostate cancer, head and neck cancer, non-small cell lung cancer, esophageal cancer, cervical cancer, neuroblastoma, gastric cancer, small-cell lung cancer, osteosarcoma, liver cancer, and biliary tract cancer. In addition, carboplatin (CAS: 41575-94-4) is presumed to be effective in cancer types such as head and neck cancer, small cell lung cancer, testicle tumor, ovarian cancer, cervical cancer, malignant lymphoma, small cell lung cancer, and breast cancer.

The dosage and frequency of administration of the platinum preparation in the present invention may be appropriately set depending on the type of drug, the condition of the patient, and the like. For example, the dose of the platinum preparation can be generally set in a range of 0.01 mg/kg/day to 100 mg/kg/day in terms of the mass of drug which is an active ingredient of the platinum preparation. The dose of the platinum preparation can be set in a range of 2 mg to 10 mg per administration in terms of the mass of drug which is an active ingredient. In addition, in a case where a commercially available platinum preparation is used, the dose of the platinum preparation may be appropriately set according to the dosage and frequency of administration described in the package insert. The dose of the platinum preparation is not limited to these dosages.

It was found in the present invention that simultaneous or sequential administration of a drug-containing liposome composition and a platinum preparation in combination has a stronger antitumor effect (for example, tumor growth inhibitory effect) as compared with every single agent (a drug-containing liposome composition or a platinum preparation).

The mechanism of action of the combined use of the liposome composition according to the embodiment of the present invention and the platinum preparation is presumed as follows, but is not limited to the following.

The liposome composition according to the embodiment of the present invention has a surprising mechanism of suppressing leakage of a drug in blood, delivering a sufficient amount of the drug to a tumor site, and rapidly releasing the drug in the tumor site. It is presumed that, due to these features of liposome formation, long-term and high-concentration drug exposure can be achieved in the tumor tissue as compared with encapsulated drugs.

On the other hand, it is said that DNA topoisomerase I is involved in the repair of DNA interstrand cross-link (DNA-ISC) which is one of DNA cross-links by the platinum preparation, in the mechanism of action of the combined use of irinotecan (topoisomerase I inhibitor) and platinum preparation (Clin Cancer Res. 1999 May; 5(5): 1189-96. Cellular pharmacology of the combination of the DNA topoisomerase I inhibitor SN-38 and the diaminocyclohexane platinum derivative oxaliplatin. Nadia Zeghari-Squalli et al.). It is presumed that, in a case where a topoisomerase I inhibitor is used in combination, DNA-ISC is difficult to be removed, the number of cells that induce apoptosis increases, and therefore a synergistic growth inhibitory effect is exerted.

Therefore, it is considered that use of the liposome composition according to the embodiment of the present invention in combination with the platinum preparation can inhibit the repair of DNA-ISC for a longer period of time and more strongly. As a result, it is presumed that the pharmaceutical formulation according to the embodiment of the present invention is a pharmaceutical formulation having a dramatically enhanced antitumor effect and low safety concerns.

The pharmaceutical formulation according to the embodiment of the present invention is a pharmaceutical formulation in which a drug-containing liposome composition and a platinum preparation are combined and administered simultaneously or sequentially, and can be preferably used as an anticancer agent.

The type of cancer to which the pharmaceutical formulation according to the embodiment of the present invention is applied is not particularly limited, and examples thereof include lung cancer (especially small cell lung cancer), ovarian cancer, pediatric solid tumor, cervical cancer, breast cancer, prostate cancer, endometrial cancer, gastric cancer (gastric adenocarcinoma), non-small cell lung cancer, pancreatic cancer, head and neck squamous cell carcinoma, esophageal cancer, bladder cancer, melanoma, colon cancer, renal cell cancer, non-Hodgkin's lymphoma, urothelial cancer, multiple myeloma, acute myeloid leukemia, chronic myeloid leukemia, acute lymphocytic leukemia, adult T cell leukemia, bone marrow metastatic cancer, sarcoma, soft tissue tumor, chronic myelomonocytic leukemia, Hodgkin's lymphoma, and cutaneous T cell lymphoma.

The resistance means that cancer cells show resistance to an anticancer agent and includes the natural resistance to which the anticancer agent does not work from the beginning of treatment and a condition in which an initially effective anticancer agent is ineffective or diminishes in effect as the treatment continues. Specifically, the resistance refers to a property that cells did not show an appropriate response to an anticancer agent in that the cells responded to the anticancer agent in the early stage, but then showed a decrease in responsiveness during the treatment, or in that the cells continued to proliferate during the treatment with the anticancer agent.

The pharmaceutical formulation according to the embodiment of the present invention can exert an excellent effect on topotecan-resistant cancer. The breast cancer resistance protein (BCRP) is a member of the ATP-binding cassette (ABC) transporter protein family. This transporter protein directs an efflux of an anticancer agent from cancer cells and reduces an intracellular concentration of the anticancer agent, thus reducing or eliminating a desired anticancer effect of the drug in these resistant cancer cells. It is speculated that the pharmaceutical formulation according to the embodiment of the present invention can exert an excellent effect on topotecan-resistant cancer by achieving exposure of tumor cells to a high concentration of topotecan over a long period of time due to the EPR effect that the drug is accumulated and retained in tumor tissues.

(Tumor Volume)

In the present invention, a tumor can be transplanted into a model animal (preferably a mouse or a rat) in order to measure the tumor volume. Inhibition of tumor volume growth depends on the drug used, the combination of lipids or the like constituting the liposome, and the effective amount. The inhibition of tumor volume growth refers to at least one of inhibiting tumor growth, achieving tumor stasis, or achieving substantial or complete tumor regression.

In a case where the liposome composition according to the embodiment of the present invention is administered to a subject such as a mammal, the administration can be started after assignment of model animals into a treatment group and a control group, and then transplantation of tumor cells into the subject animals, for example, growth of the tumor cells to 100 to 1,000 μm such that the tumor cells settle.

For example, in a case where the model animal is a mouse, mice in each group can be weighed as a whole daily until the animals reach a minimum body weight, as an evaluation of the liposome composition according to the embodiment of the present invention.

Tumors can be measured with calipers or the like until the final sacrifice of the animals for sampling, until tumors reach 2,000 mm$^3$, or until the animals die. The tumor volume in a mammalian subject can be measured using any method recognized in the related art.

For example, caliper measurement can be used to evaluate the tumor volume using the expression: $(a \times b^2) \times 0.5$, where "a" is a maximum diameter and "b" is a minor axis length. In addition, in a case of humans, the tumor volume can be measured by a technique for diagnostic imaging such as computer tomography (CT) scanning or magnetic resonance imaging (MRI) scanning.

EXAMPLES

Hereinafter, the present invention will be specifically described with reference to Examples, but the present invention is not limited thereto. It is understood that the present invention can be variously changed and modified by those skilled in the art. Unless such changes and modifications depart from the scope of the present invention, those changes and modifications are included in the present invention. Various reagents used in the Examples are commercially available unless otherwise specified.

SM represents sphingomyelin (COATSOME NM-10, manufactured by NOF Corporation).

Chicken egg-derived DHSM represents dihydrosphingomyelin obtained by hydrogenating chicken egg-derived SM (synthetic product obtained by hydrogenating COATSOME NM-10 (manufactured by NOF Corporation)). This chicken egg-derived DHSM is a mixture containing DHSM having two alkyl chains having 16 carbon atoms, which accounts for 70% to 80% of a total of the chicken egg-derived DHSM, and DHSM having different alkyl chain lengths, which is the remainder.

Totally synthetic DHSM represents dihydrosphingomyelin produced by chemical synthesis so as to contain 98% or more of the following compound having a long-chain alkyl group having 16 carbon atoms and a long-chain alkyl group having 18 carbon atoms.

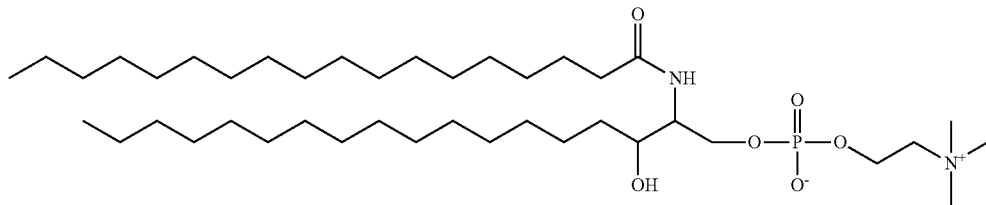

SUNBRIGHT DSPE-020CN (hereinafter referred to as DSPE-PEG, manufactured by NOF Corporation) was used as PEG phospholipid (denoted as PEG in the table).

Cholesterol HP (manufactured by Nippon Fine Chemical Co., Ltd.) was used as cholesterol (denoted as Chol in the table).

Comparative Examples 1 to 10

(a) Preparation of Oil Phase

For Comparative Example 1, 11.52 g of SM, 4.32 g of PEG phospholipid, and 4.32 g of cholesterol were respectively weighed. For Comparative Examples 2 to 10, the amounts of SM or chicken egg-derived DHSM, PEG phospholipid, and cholesterol were changed to the ratios described in Table 1. The lipids were mixed with 381 mL of ethanol and dissolved at 65° C. to prepare an oil phase.

(b1) Preparation of Water Phase 1

25.2 g of ammonium sulfate was dissolved in 1118.5 g of water to prepare water phase 1.

(b2) Preparation of Water Phase 2

5.04 g of ammonium sulfate was dissolved in 223.7 g of water to prepare water phase 2.

(c) Formation of Liposome Particles by Emulsification

The water phase 1 prepared in (b1) was heated to 65° C., the whole of the oil phase prepared in (a) was added thereto, and then these phases were mixed with a precision emulsification disperser at a circumferential speed of 26 m/s for 60 minutes. Subsequently, the water phase 2 at room temperature was added thereto, followed by continuing the stirring at a circumferential speed of 0.1 m/s while heating at 65° C. to evaporate the organic solvent and water. In a case where the liquid was concentrated to 600 mL, the heating and stirring were stopped and therefore the evaporation was terminated.

(e) Replacement of Liposome Outer Water Phase Liquid by Dialysis

An aqueous solution of 3.15% by mass of NaCl was used as a dialysis liquid. Using this dialysis liquid, the liquid obtained in (c) was subjected to cross-flow filtration at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to make 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 60 minutes.

(g) Removal of Outer Water Phase Topotecan by Dialysis

A sucrose/histidine buffer solution consisting of 9.4% by mass of sucrose and 10 mmol/L of histidine was prepared as a dialysis liquid. Using this dialysis liquid, the liquid obtained in (f) was subjected to cross-flow filtration at room temperature to remove topotecan present in the outer water phase to obtain topotecan-containing liposomes in which the outer water phase was replaced with the dialysis liquid.

Comparative Examples 11 and 12

(a) Preparation of Oil Phase

For Comparative Example 11, 0.517 g of chicken egg-derived DHSM and 0.233 g of cholesterol were respectively weighed. For Comparative Example 12, the amounts of SM and cholesterol were changed to the ratios described in Table 1. In order to label liposomes with DiI (1,1'-dioctadecyl-3,3,3',3'-tetramethylindocarbocyanine perchlorate), an amount of DiI, which was 0.2 mol % with respect to total lipids, was weighed and dissolved in ethanol. Ethanol was added to the DiI ethanol solution to make a total volume of 1.5 mL, and the weighed lipid and this organic solvent were mixed and heated to 65° C. to dissolve the lipid and form an oil phase.

(b) Preparation of Water Phase 0.9 g of ammonium sulfate and 2.16 g of sucrose were dissolved in 13.5 g of water to prepare a water phase.

(c) Formation of Liposome Particles by Mixing Oil Phase and Water Phase

The water phase prepared in (b) was heated to 65° C. and stirred with a magnetic stirrer (3,000 rpm). The whole oil phase prepared in (a) was heated to 65° C. with a hot plate, and the whole oil phase was sucked with a syringe and heated for 5 minutes with a hot plate. The oil phase was added dropwise over 30 seconds to the heated water phase.

(d) Particle Size Regulation by Extruder

The liquid obtained in (c) was subjected to the particle size regulation by sequentially passing it through a filter using an extruder (Mini Extruder, manufactured by Avanti Polar Lipids, Inc.) under heating at 70° C.

(e) Replacement of Liposome Outer Water Phase Liquid by Dialysis

An aqueous solution of 0.09% by mass of NaCl was used as a dialysis liquid. Using this dialysis liquid, the liquid obtained in (c) or (d) was subjected to dialysis at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to make 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 120 minutes.

(g) Removal of Outer Water Phase Topotecan by Dialysis

A sucrose/histidine buffer solution consisting of 9.4% by mass sucrose and 10 mmol/L histidine was prepared as a dialysis liquid. Using this dialysis liquid, the liquid obtained in (f) was subjected to dialysis at room temperature to remove topotecan present in the outer water phase to obtain topotecan-containing liposomes in which the outer water phase was replaced with the dialysis liquid.

Examples 1 to 8

(a) Preparation of Oil Phase

For Example 1, 11.52 g of chicken egg-derived DHSM, 4.32 g of PEG phospholipid (SUNBRIGHT DSPE-020CN, manufactured by NOF Corporation, hereinafter referred to as DSPE-PEG), and 4.32 g of cholesterol were respectively weighed. For Examples 2 to 8, the amounts of DHSM, DSPE-PEG, and cholesterol were changed to the ratios described in Table 2. The lipids were mixed with 381 mL of ethanol and dissolved at 65° C. to prepare an oil phase.

(b1) Preparation of Water Phase 1

25.2 g of ammonium sulfate was dissolved in 1118.5 g of water to prepare water phase 1.

(b2) Preparation of Water Phase 2

5.04 g of ammonium sulfate was dissolved in 223.7 g of water to prepare water phase 2.

(c) Formation of Liposome Particles by Emulsification

The water phase 1 prepared in (b1) was heated to 65° C., the whole of the oil phase prepared in (a) was added thereto, and then these phases were mixed with a precision emulsification disperser at a circumferential speed of 26 m/s for 60 minutes. Subsequently, the water phase 2 at room temperature was added thereto, followed by continuing the stirring at a circumferential speed of 0.1 m/s while heating at 65° C. to evaporate the organic solvent and water. In a case where the liquid was concentrated to 600 mL, the heating and stirring were stopped and therefore the evaporation was terminated.

(e) Replacement of Liposome Outer Water Phase Liquid by Dialysis

An aqueous solution of 3.15% by mass of NaCl was used as a dialysis liquid. Using this dialysis liquid, the liquid obtained in (c) was subjected to cross-flow filtration at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to make 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 60 minutes.

(g) Removal of Outer Water Phase Topotecan by Dialysis

A sucrose/histidine buffer solution consisting of 9.4% by mass of sucrose and 10 mmol/L of histidine was prepared as a dialysis liquid. Using this dialysis liquid, the liquid obtained in (f) was subjected to cross-flow filtration at room temperature to remove topotecan present in the outer water phase to obtain topotecan-containing liposomes in which the outer water phase was replaced with the dialysis liquid.

Examples 9 and 10

(a) Preparation of Oil Phase

For Example 9, 0.412 g of chicken egg-derived DHSM, 0.153 g of DSPE-PEG, and 0.153 g of cholesterol were respectively weighed. For Example 10, the amounts of chicken egg-derived DHSM, DSPE-PEG, and cholesterol were changed to the ratios described in Table 2. In order to label liposomes with DiI, an amount of DiI, which was 0.2 mol % with respect to total lipids, was weighed and dissolved in ethanol. Ethanol was added to the resulting DiI ethanol solution to make a total volume of 11.25 mL, and 3.75 mL of ethyl acetate was further added thereto. The weighed lipid and this organic solvent were mixed and heated to 60° C. to dissolve the lipid, thus preparing an oil phase.

(b) Preparation of Water Phase 0.9 g of ammonium sulfate was dissolved in 40 g of water to prepare a water phase.

(c) Formation of Liposome Particles by Emulsification

The water phase prepared in (b) was heated to 70° C., the whole of the oil phase prepared in (a) was added thereto (volume ratio: water phase/oil phase=8/3), and then these phases were mixed using an emulsification machine (Excel Auto homogenizer ED-3, manufactured by Nihonseiki Kaisha Ltd.) at 3,000 rpm (rotation per minute: $\frac{1}{60}s^{-1}$) for 30 minutes. This was followed by continuing the stirring at 300 rpm while heating at 65° C. to evaporate the organic solvent and water. In a case where the liquid was concentrated to 15 g, the heating and stirring were stopped and therefore the evaporation was terminated.

(d) Particle Size Regulation by Extruder

The liquid obtained in (c) was subjected to the particle size regulation by sequentially passing it through a filter using an extruder (Mini Extruder, manufactured by Avanti Polar Lipids, Inc.) under heating at 70° C.

(e) Replacement of Liposome Outer Water Phase Liquid by Dialysis

An aqueous solution of 0.09% by mass of NaCl was used as a dialysis liquid. Using this dialysis liquid, the liquid obtained in (c) or (d) was subjected to dialysis at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to make 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 120 minutes.

(g) Removal of Outer Water Phase Topotecan by Dialysis

A sucrose/histidine buffer solution consisting of 9.4% by mass of sucrose and 10 mmol/L of histidine was prepared as a dialysis liquid. Using this dialysis liquid, the liquid obtained in (f) was subjected to dialysis at room temperature to remove topotecan present in the outer water phase to obtain topotecan-containing liposomes in which the outer water phase was replaced with the dialysis liquid.

[Measurement and Evaluation of Physical Properties]

<Average Particle Size>

In the present invention, the average particle size refers to a cumulant average particle size measured by a dynamic light scattering method. The average particle size in each of Examples and Comparative Examples described in the tables is a cumulant average particle size measured by a dynamic light scattering method using a Fiber-Optics Particle Analyzer with Auto-sampler FPAR-1000AS (manufactured by Otsuka Electronics Co., Ltd.). The measurement results are shown in Tables 1 and 2.

<Topotecan Concentration Measurement>

Tables 1 and 2 show the results of quantifying the concentration of topotecan by measuring a sample with a high performance liquid chromatography (HPLC) apparatus Nexera-i LC-2040C (manufactured by Shimadzu Corporation). The specific measurement method is as follows.

In the liposomes of Tables 1 and 2, the percentage of the drug contained in the inner water phase of the liposome to the drug in the entire liposome composition was at least 95%, except for Comparative Example 10. For Comparative Example 10, the percentage of the drug contained in the inner water phase of the liposome to the drug in the entire liposome composition was 59%.

Measurement of Amount of Topotecan in Liposome Preparation

The prepared liposome liquid was dissolved in methanol and then filtered to prepare a sample solution, and topotecan hydrochloride was diluted to prepare a calibration curve standard solution. Using the sample solution and the calibration curve standard solution thus prepared, the amount of topotecan in liposome preparation was measured by liquid chromatography/UV-vis absorbance detection.

The concentration of topotecan in the inner water phase was calculated by subtracting the concentration of topotecan in the outer water phase from the concentration of topotecan in the entire water phase.

The concentration of topotecan in each water phase was measured as follows.

(Concentration of Topotecan in Entire Water Phase)

50 µL of the liposome dispersion liquid was measured and 950 µL of methanol was added thereto, followed by stirring with a vortex for 1 minute. 100 µL of the liquid was measured and 900 µL of Milli-Q water was added thereto, followed by stirring with a vortex for 1 minute to prepare a sample for HPLC analysis.

(Concentration of Topotecan in Outer Water Phase)

50 µL of the liposome dispersion liquid was measured and then diluted by adding 450 µl of a 9.4 wt % sucrose/10 mM histidine aqueous solution. 200 µL of PBS was added to 100 µL of the liquid which was then mixed by inversion. The dispersion liquid was ultracentrifuged (200,000 g, 20° C., 60 minutes), and the supernatant was used as an HPLC analysis sample. The ultracentrifuge used was Himac CP80WX (manufactured by Hitachi, Ltd).

a) Preparation of Calibration Curve Standard Solution

About 20 mg of topotecan hydrochloride was weighed and dissolved in 20 mL of 10% by mass methanol aqueous solution. Milli-Q water was added to this liquid to prepare solutions having a topotecan hydrochloride concentration of 0.1, 1.0, 5.0, 10.0, 20.0, 50.0, or 100.0 ppm, which were then used as a calibration curve standard solution.

b) Preparation of Sample Solution (1) About 50 µL of a sample (liposome preparation solution) was weighed by MICROMAN (registered trademark), and about 950 µL of methanol weighed by MICROMAN was added thereto. After it was shaken for about 1 minute, the solution was visually confirmed to become clear.

(2) 100 µL of the solution of the above (1) was weighed by MICROMAN, and about 900 µL of Milli-Q water weighed by a micropipette was added thereto. This liquid was shaken for about 1 minute, sonicated for about 1 minute, and further shaken for about 10 seconds.

(3) The solution obtained by filtering the solution of the above (2) through a DISMIC (registered trademark) filter (pore diameter: 0.45 µm) was used as a sample solution.

c) Measurement

The measurement was carried out under the following conditions by liquid chromatography/UV-vis absorbance detection.

Measurement wavelength: 382 nm, column: Shiseido CAPCELLPAK C18 ACR 3 µm_3.0 mm*75 mm Column temperature: constant temperature of around 40° C.

Mobile phases A and B were both water/methanol/trifluoroacetic acid mixtures, and feeding of the mobile phases was carried out by changing the mixing ratio of mobile phases A and B to control a concentration gradient.

Measurement was carried out under the conditions of a flow rate: 1.0 mL/minute, an injection volume: 10 µL, and an autosampler temperature: a constant temperature of around 25° C.

<Measurement of Sulfate Ion Concentration>

The sample was measured with an ion chromatography apparatus 883 Basic IC plus (manufactured by Metrohm AG) to quantify the concentration of sulfate ions. The results of measuring the molar ratio of sulfate ions to topotecan are shown in Tables 1 and 2. In the liposomes of Tables 1 and 2, the percentage of sulfate ions contained in the inner water phase of the liposome to sulfate ions in the entire liposome composition was at least 90%.

The concentration of sulfate ions in the inner water phase was calculated by subtracting the concentration of sulfate ions in the outer water phase from the concentration of sulfate ions in the entire water phase. The concentration of sulfate ions in each water phase was measured as follows.

(Concentration of Sulfate Ions in Entire Water Phase)

50 µL of the liposome dispersion liquid was measured and 950 µL of methanol was added thereto, followed by mixing with ultrasonication for 15 seconds. 90 µL of the liquid was measured and 810 µL of water for injection (manufactured by Hikari Pharmaceutical Co., Ltd.) was added thereto, followed by mixing with ultrasonication for 30 seconds. 900 µL of ethyl acetate was added to the resulting solution which was then shaken well to extract lipids into an ethyl acetate phase. An appropriate amount of the water phase liquid was measured and used for ion chromatography analysis.

(Concentration of Sulfate Ions in Outer Water Phase)

100 µL of the liposome dispersion liquid was measured and then diluted by adding 900 µL of 5% glucose solution (manufactured by Otsuka Pharmaceutical Co., Ltd.). 450 µL of the resulting liquid was treated by ultrafiltration, and the filtrate was used as an ion chromatography analysis sample.

The centrifugation conditions were 7,400 g, 5° C., and 30 minutes. The centrifuge used was Himac CF15RXII (manufactured by Hitachi, Ltd).

<Measurement of AUC>

The mice to which the prepared topotecan-containing liposomes were administered (dose: 1 mg/kg in terms of the amount of drug) were bled at 0.25, 2, 6, and 24 hours after administration. The blood was centrifuged at 800×g for 10 minutes to recover plasma. The concentration of topotecan was quantified for the collected plasma using liquid chromatography/mass spectrometry/mass spectrometry (LC/MS/MS). Using the pharmacokinetic analysis software WinNonlin (registered trademark) (available from Certara, L.P.), the area under blood concentration-time curve (AUC) up to infinite time after single administration was calculated from the transition of the topotecan concentration thus obtained. The unit of AUC is time×ng/mL (expressed as hr*ng/mL in the table). In addition, the AUC of the liposome described in literature [AACR-EORTC International Conference, San Francisco, California, Oct. 22-26, 2007, #C113 A Pharmacokinetics Study of a Novel Sphingomyelin/Cholesterol Liposomal Topotecan and Non-Liposomal Topotecan in Rats, William C. Zamboni et al.] is calculated to be 68152 hr×ng/mL.

in the inner water phase to the drug in the entire water phase is less than 0.36, and Comparative Examples 11 and 12 in which hydrophilic polymer-modified diacylphosphatidyle-

TABLE 1

| | Average particle size nm | Concentration of topotecan in entire water phase ppm | $SO_4^{2-}$ in inner water phase/topotecan in entire water phase mol/mol | Molar ratio of constitutional components of liposome membrane | | | | Dose mg/kg | AUC hr * ng/ml | Percentage of topotecan in inner water phase % | Percentage of $SO_4^{2-}$ in inner water phase % |
|---|---|---|---|---|---|---|---|---|---|---|---|
| | | | | PEG | Chol | DHSM | SM | | | | |
| Comparative Example 1 | 101.7 | 2419 | 0.70 | 4.7% | 37% | 0% | 58% | 1.0 | 120189 | 99 | 100 |
| Comparative Example 2 | 96.3 | 2605 | 0.75 | 4.8% | 42% | 0% | 53% | 1.0 | 136669 | 100 | 100 |
| Comparative Example 3 | 90.2 | 2993 | 1.57 | 4.5% | 42% | 0% | 54% | 1.0 | 140108 | 100 | 98 |
| Comparative Example 4 | 105.2 | 2889 | 1.58 | 4.6% | 47% | 0% | 48% | 1.0 | 137082 | 100 | 98 |
| Comparative Example 5 | 91.1 | 2946 | 1.01 | 4.9% | 47% | 0% | 48% | 1.0 | 157878 | 100 | 96 |
| Comparative Example 6 | 99.3 | 2994 | 1.01 | 4.7% | 39% | 0% | 56% | 1.0 | 143615 | 100 | 100 |
| Comparative Example 7 | 101.2 | 3080 | 0.96 | 4.7% | 39% | 0% | 56% | 1.0 | 119518 | 100 | 98 |
| Comparative Example 8 | 100.8 | 2437 | 1.14 | 4.7% | 39% | 0% | 57% | 1.0 | 173179 | 100 | 98 |
| Comparative Example 9 | 90.8 | 1191 | 0.32 | 5.0% | 38% | 57% | 0% | 1.0 | 140277 | 100 | 100 |
| Comparative Example 10 | 131.2 | 1328 | 0.3 | 4.4% | 36% | 59% | 0% | 1.0 | 174087 | 59 | 100 |
| Comparative Example 11 | 106 | 1876 | — | 0% | 43% | 57% | 0% | 1.0 | 182694 | 99 | — |
| Comparative Example 12 | 111.2 | 2437 | — | 0% | 45% | 0% | 55% | 1.0 | 134591 | 100 | — |

TABLE 2

| | Average particle size nm | Concentration of topotecan in entire water phase ppm | $SO_4^{2-}$ in inner water phase/topotecan in entire water phase mol/mol | Molar ratio of constitutional components of liposome membrane | | | | Dose mg/kg | AUC hr * ng/ml | Percentage of topotecan in inner water phase % | Percentage of $SO_4^{2-}$ in inner water phase % |
|---|---|---|---|---|---|---|---|---|---|---|---|
| | | | | PEG | Chol | DHSM | SM | | | | |
| Example 1 | 100 | 2160 | 0.66 | 5.6% | 40% | 54% | 0% | 1.0 | 227895 | 99 | 97 |
| Example 2 | 122 | 2347 | 1.38 | 5.3% | 39% | 56% | 0% | 1.0 | 201264 | 100 | 100 |
| Example 3 | 88 | 2353 | 1.16 | 5.4% | 38% | 56% | 0% | 1.0 | 270579 | 99 | 100 |
| Example 4 | 111.3 | 2167 | 1.05 | 5.2% | 38% | 57% | 0% | 1.0 | 295476 | 99 | 98 |
| Example 5 | 115.9 | 2659 | 0.8 | 5.1% | 35% | 60% | 0% | 1.0 | 330913 | 100 | 100 |
| Example 6 | 125.2 | 1349 | 0.9 | 4.4% | 36% | 60% | 0% | 1.0 | 261345 | 99 | 100 |
| Example 7 | 120.3 | 3984 | 0.6 | 5.0% | 43% | 52% | 0% | 1.0 | 278684 | 98 | 98 |
| Example 8 | 116.8 | 2254 | 1.1 | 5.1% | 43% | 52% | 0% | 1.0 | 307412 | 99 | 98 |
| Example 9 | 101 | 1561 | 0.73 | 10.0% | 40% | 50% | 0% | 1.0 | 245450 | 100 | 100 |
| Example 10 | 104 | 1758 | 0.68 | 5.1% | 40% | 55% | 0% | 1.0 | 270294 | 100 | 92 |

As can be seen from the results in Tables 1 and 2, in Examples 1 to 10 of the liposome composition including a hydrophilic polymer-modified diacylphosphatidyletha-nolamine, a dihydrosphingomyelin, and cholesterol as constitutional components of a liposome membrane, in which an inner water phase contains ammonium sulfate, and a molar ratio of sulfate ions in the inner water phase to the drug in the entire water phase is 0.36 or more, it was shown that the measured value of AUC is 200,000 or more and therefore high retention in blood can be achieved.

On the other hand, in Comparative Examples 1 to 8 in which dihydrosphingomyelin is not used, Comparative Examples 9 and 10 in which the molar ratio of sulfate ions thanolamine is not used, it was shown that the measured value of AUC is less than 200,000, which is inferior to Examples 1 to 10.

(Composition of Topotecan-Containing Liposome Composition (Hereinafter, Also Referred to as Topotecan-Containing Liposome Composition According to Embodiment of Present Invention or Lipo))

Topotecan hydrochloride: 20 mg
HSPC (Note 1): 95.8 mg
MPEG-DSPE (Note 2): 31.9 mg
Cholesterol: 31.9 mg
Ammonium sulfate: 20 mg
L-histidine: 15.5 mg Purified white sugar: 940 mg
pH adjusting agent: q.s.
(Physical Properties of Topotecan-Containing Liposome Composition)

It was confirmed that the molar ratio of sulfate ions in the inner water phase to the drug in the entire water phase was 0.36 or more.

Carboplatin (available from Tokyo Chemical Industry Co., Ltd.) was used as the platinum preparation.

The 10 mM histidine/9.4% sucrose solution is a solution in which the concentration of histidine is 10 mM in an aqueous solution containing 9.4 g/100 mL of sucrose.

Paclitaxel was obtained from Shonan Wako Junyaku K.K.

A2780 cells were obtained from the ECACC cell bank.
(Drug Efficacy Test with Combined Use of Platinum Preparation in Tumor-Bearing Mouse Model with Subcutaneous Transplantation of A2780)

A platinum preparation (hereinafter, also referred to as carboplatin), the topotecan-containing liposome composition according to the embodiment of the present invention, and paclitaxel were used as test substances. Physiological saline (available from Otsuka Pharmaceutical Factory, Inc., hereinafter, also referred to as carboplatin solvent) was used for the dilution of carboplatin. A 10 mM histidine/9.4% sucrose solution (hereinafter, also referred to as Lipo solvent) was used for the dilution of Lipo. 12.5% CREMOPHOR (available from Sigma-Aldrich, LLC)/12.5% ethanol (available from Shonan Wako Junyaku K.K.)/75% physiological saline (available from Otsuka Pharmaceutical Factory, Inc.) was used for the dilution of paclitaxel.

$5 \times 10^6$ A2780 cells, which is a human ovarian cancer cell line, were subcutaneously transplanted into the flank of female BALB/cAJcl-nu/nu mice to form subcutaneous tumors. From 7 days after transplantation, mice were drug treated with carboplatin alone, Lipo of the present invention alone, a combination of carboplatin and Lipo, and a combination of carboplatin and paclitaxel, and the effect of the drug treatment on the survival time of the mice was evaluated. In a case where a volume of tumor reached 2,000 mm³ or in a case where significant deterioration of the condition was observed, the animals were euthanized and considered dead.

In the combination group of a carboplatin solvent and a Lipo solvent, the carboplatin solvent was administered by intraperitoneal administration, and the Lipo solvent was administered by tail vein administration once a week for 2 weeks. The carboplatin alone group was administered by intraperitoneal administration once a week for 2 weeks. The Lipo alone group was administered by tail vein administration once a week for 2 weeks. In the combination group of carboplatin and Lipo, carboplatin was administered as a single dose by intraperitoneal administration, and Lipo was administered as a single dose by tail vein administration. In the combination group of carboplatin and paclitaxel, carboplatin was administered as a single dose by intraperitoneal administration, and paclitaxel was administered as a single dose by tail vein administration.

With Regard to a Group Configuration,

Group 1 was a group with the administration of the carboplatin solvent and the solvent of the topotecan-containing liposome composition according to the embodiment of the present invention, Group 2 was a group with the administration of carboplatin (80 mg/kg), Group 3 was a group with the administration of the topotecan-containing liposome composition according to the embodiment of the present invention (0.5 mg/kg), Group 4 was a group with the administration of carboplatin (80 mg/kg) and the topotecan-containing liposome composition according to the embodiment of the present invention (0.5 mg/kg), and Group 5 was a group with the administration of carboplatin (80 mg/kg) and paclitaxel (20 mg/kg).

Groups 1 to 3 and 5 correspond to Comparative Examples, and Group 4 corresponds to Example. The group configuration and dose are shown in Table 3. In Table 3, "Lipo" represents the topotecan-containing liposome composition according to the embodiment of the present invention, "Abdomen" represents intraperitoneal administration, "Tail" represents tail vein administration, "Once a week×2" represents administration once a week for 2 weeks, and "Once" represents administration once during the test period.

Table 4 shows a median survival time calculated from the start of drug administration. FIG. 1 shows changes in a survival rate of each group.

|       |                               | Dose (mg/kg/administration) |      |            | Carboplatin and carboplatin solvent |                  | Lipo, Lipo solvent, and paclitaxel |                  |                   |
|-------|-------------------------------|-----------------------------|------|------------|-------------------------------------|------------------|------------------------------------|------------------|-------------------|
| Group | Test substance                | Carboplatin                 | Lipo | Paclitaxel | Administration route                | Administration schedule | Administration route         | Administration schedule | Dosage (mL/kg) |
| 1     | Carboplatin solvent + Lipo solvent | 0                       | 0    | —          | Abdomen                             | Once a week × 2  | Tail vein                          | Once a week × 2  | 10                |
| 2     | Carboplatin                   | 80                          | —    | —          | Abdomen                             | Once a week × 2  | —                                  | —                | 10                |
| 3     | Lipo                          | —                           | 0.5  | —          | —                                   | —                | Tail vein                          | Once a week × 2  | 10                |
| 4     | Carboplatin + Lipo            | 80                          | 0.5  | —          | Abdomen                             | Once              | Tail vein                          | Once              | 10                |
| 5     | Carboplatin + paclitaxel      | 80                          | —    | 20         | Abdomen                             | Once              | Tail vein                          | Once              | 10                |

TABLE 4

| Group | Median survival time (days) | Number of animals in group | Number of animal deaths or euthanasias due to deterioration of condition |
|-------|-----------------------------|----------------------------|--------------------------------------------------------------------------|
| 1     | 7                           | 8                          | 0                                                                        |
| 2     | 10                          | 8                          | 1                                                                        |
| 3     | 17                          | 8                          | 0                                                                        |
| 4     | 24                          | 8                          | 0                                                                        |
| 5     | 9.5                         | 8                          | 5                                                                        |

Group 4 showed a significant survival prolonging effect compared to Group 1, Group 2, Group 3, or Group 5 (P<0.05, stratified Log-rank test). Death or euthanasia due to deterioration of the condition occurred in 5 of 8 animals in Group 5, while the number of animal deaths or euthanasias due to deterioration of the condition was 0 in Group 4.

From the above results, the topotecan-containing liposome composition according to the embodiment of the present invention, in a case of being used in combination with carboplatin, showed a significant survival prolonging effect relative to the topotecan-containing liposome composition according to the embodiment of the present invention alone, carboplatin alone, or a combination of carboplatin and paclitaxel, which is a standard therapy for ovarian cancer. In addition, high safety was confirmed.

(Drug Efficacy Test with Combined Use of Platinum Preparation in Tumor-Bearing Mouse Model with Subcutaneous Transplantation of A2780)

A platinum preparation (hereinafter, also referred to as carboplatin), the topotecan-containing liposome composition according to the embodiment of the present invention, and topotecan were used as test substances. Physiological saline (available from Otsuka Pharmaceutical Factory, Inc., hereinafter, also referred to as carboplatin solvent) was used for the dilution of carboplatin and topotecan. A 5% Otsuka glucose solution (available from Otsuka Pharmaceutical Factory, Inc., hereinafter, also referred to as Lipo solvent) was used for the dilution of Lipo.

$5 \times 10^6$ A2780 cells, which is a human ovarian cancer cell line, were subcutaneously transplanted into the flank of female BALB/cAJcl-nu/nu mice to form subcutaneous tumors. From 7 days after transplantation, mice were drug treated with carboplatin alone, Lipo of the present invention alone, topotecan alone, a combination of carboplatin and Lipo, and a combination of carboplatin and topotecan, and the effect of the drug treatment on the survival time of the mice was evaluated. In a case where a volume of tumor reached 2,000 $mm^3$ or in a case where significant deterioration of the condition was observed, the animals were euthanized and considered dead.

In the combination group of a carboplatin solvent and a Lipo solvent, the carboplatin solvent was administered by intraperitoneal administration, and the Lipo solvent was administered by tail vein administration once a week for 2 weeks. The carboplatin alone group was administered by intraperitoneal administration once a week for 2 weeks. The Lipo alone group was administered by tail vein administration once a week for 2 weeks. In the combination group of carboplatin and Lipo, carboplatin was administered by intraperitoneal administration once a week for 2 weeks, and Lipo was administered by tail vein administration once a week for 2 weeks. In the combination group of carboplatin and topotecan, carboplatin was administered as a single dose by intraperitoneal administration, and topotecan was administered by tail vein administration once a day for 5 days.

With Regard to a Group Configuration,

Group 1 was a group with the administration of the carboplatin solvent and the solvent of the topotecan-containing liposome composition according to the embodiment of the present invention, Group 2 was a group with the administration of carboplatin (80 mg/kg), Group 3 was a group with the administration of the topotecan-containing liposome composition according to the embodiment of the present invention (0.5 mg/kg), Group 4 was a group with the administration of topotecan (0.5 mg/kg), Group 5 was a group with the administration of carboplatin (80 mg/kg) and the topotecan-containing liposome composition according to the embodiment of the present invention (0.5 mg/kg), and Group 6 was a group with the administration of carboplatin (80 mg/kg) and topotecan (0.5 mg/kg).

Groups 1 to 4 and 6 correspond to Comparative Examples, and Group 5 corresponds to Example. The group configuration and dose are shown in Table 5. In Table 5, "Lipo" represents the topotecan-containing liposome composition according to the embodiment of the present invention, "Abdomen" represents intraperitoneal administration, "Tail" represents tail vein administration, "Once a week×2" represents once a week for 2 weeks, "Once a day×5" represents administration once a day for 5 days, and "Once" represents administration once during the test period.

Figure 2:
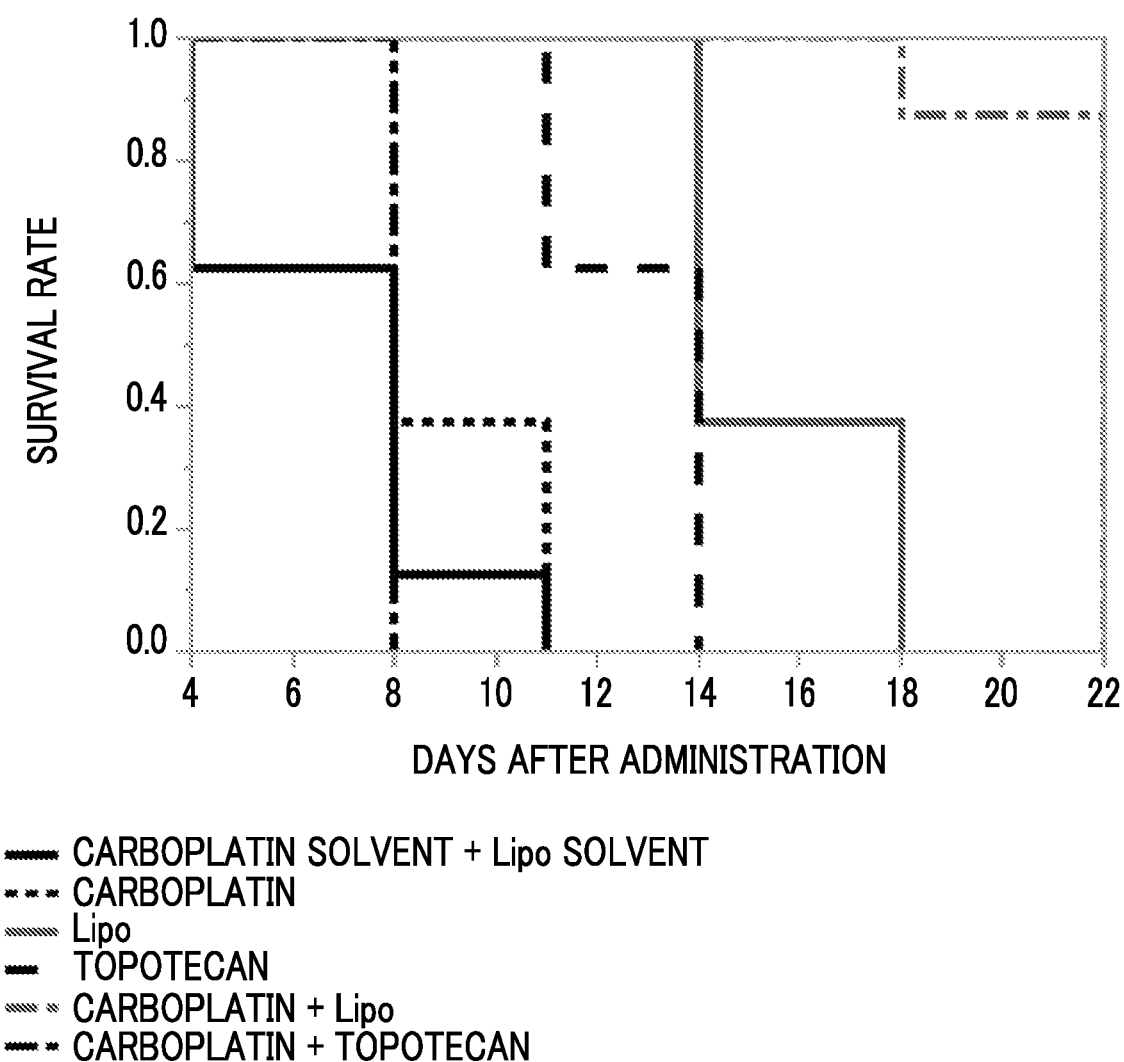
FIG. 2 shows a survival curve in a drug efficacy test using a tumor-bearing mouse model with subcutaneous transplantation of A2780.

Table 6 shows a median survival time calculated from the start of drug administration. FIG. 2 shows changes in a survival rate of each group.

| Group | Test substance | Dose (mg/kg/administration) Carboplatin | Lipo | Topotecan | Administration route | Carboplatin and carboplatin solvent Administration schedule | Administration (mL/kg) | Lipo, Lipo solvent, and topotecan Administration schedule | Dosage (mL/kg) |
|---|---|---|---|---|---|---|---|---|---|
| 1 | Carboplatin solvent + Lipo solvent | 0 | 0 | — | Abdomen | Once a week × 2 | Tail vein | Once a week × 2 | 10 |
| 2 | Carboplatin | 80 | — | — | Abdomen | Once a week × 2 | — | — | 10 |
| 3 | Lipo | — | 0.5 | — | — | — | Tail vein | Once a week × 2 | 10 |
| 4 | Topotecan | — | — | 0.5 | — | — | Tail vein | Once a day × 5 | 10 |
| 5 | Carboplatin + Lipo | 80 | 0.5 | — | Abdomen | Once a week × 2 | Tail vein | Once a week × 2 | 10 |
| 6 | Carboplatin + topotecan | 80 | — | 0.5 | Abdomen | Once | Tail vein | Once a day × 5 | 10 |

TABLE 6

| Group | Median survival time (days) | Number of animals in group | Number of animal deaths or euthanasias due to deterioration of condition |
|---|---|---|---|
| 1 | 6.9 | 8 | 0 |
| 2 | 9.1 | 8 | 0 |
| 3 | 15.5 | 8 | 0 |
| 4 | 12.9 | 8 | 0 |
| 5 | 21.5 | 8 | 0 |
| 6 | 8.0 | 8 | 8 |

Group 5 showed a significant survival prolonging effect compared to Group 1, Group 2, Group 3, Group 4, or Group 6 ($P<0.05$, stratified Log-rank test). Death or euthanasia due to deterioration of the condition occurred in 8 of 8 animals in Group 6, while the number of animal deaths or euthanasias due to deterioration of the condition was 0 in Group 5.

The pharmaceutical formulation according to the embodiment of the present invention is useful as a pharmaceutical formulation for preventing or treating cancer. The administration method according to the embodiment of the present invention is useful as a method for administering a pharmaceutical formulation for preventing or treating cancer. Furthermore, the treatment method according to the embodiment of the present invention is useful as a treatment method for preventing or treating cancer.

What is claimed is:

1. A method for treating a cancer of a subject, consisting of:
   simultaneously or sequentially administering (A) a liposome composition in combination with (B) a platinum preparation at an effective dose and for a dosing period in which the subject exhibits a therapeutic synergistic effect,
   in which the liposome composition includes, as constitutional components of a liposome membrane, a hydrophilic polymer-modified diacylphosphatidylethanolamine; a dihydrosphingomyelin; and cholesterols, the liposome composition including a drug consisting of topotecan or a salt thereof and having an inner water phase containing ammonium sulfate, and a molar ratio of sulfate ions in the inner water phase to the drug in an entire water phase is 0.36 or more,
   wherein the platinum preparation is not included in the liposome composition.

2. The method according to claim 1,
   wherein the molar ratio of the sulfate ions in the inner water phase to the drug in the entire water phase is 0.6 or more and 1.8 or less.

3. The method according to claim 1,
   wherein the hydrophilic polymer-modified diacylphosphatidylethanolamine is a polyethylene glycol- or methoxy polyethylene glycol-modified diacylphosphatidylethanolamine.

4. The method according to claim 1,
   wherein a percentage of the hydrophilic polymer-modified diacylphosphatidylethanolamine in the constitutional components of the liposome membrane is 2 to 10 mol %.

5. The method according to claim 1,
   wherein a percentage of the cholesterols in the constitutional components of the liposome membrane is 35 to 43 mol %.

6. The method according to claim 1,
   wherein a particle size is 150 nm or less.

7. The method according to claim 1,
   wherein an outer water phase has a pH of 5.5 to 8.5.

8. The method according to claim 1,
   wherein the dihydrosphingomyelin is a dihydrosphingomyelin containing a long-chain alkyl group having 16 carbon atoms and a long-chain alkyl group having 18 carbon atoms.

9. The method according to claim 1,
   wherein a drug release rate from a liposome in plasma having an ammonium concentration of 1 mmol/L or less is 20%/24 hours or less at 37° C., and a drug release rate from a liposome in plasma having an ammonium concentration of 4 to 6 mmol/L is 60%/24 hours or more at 37° C.

10. The method according to claim 1,
    wherein the platinum preparation includes at least one selected from carboplatin, cisplatin, oxaliplatin, or nedaplatin.

11. A method for treating a cancer of a subject, consisting essentially of:
    simultaneously or sequentially administering (A) a liposome composition in combination with (B) a platinum preparation at an effective dose and for a dosing period in which the subject exhibits a therapeutic synergistic effect,
    in which the liposome composition includes, as constitutional components of a liposome membrane, a hydrophilic polymer-modified diacylphosphatidylethanolamine; a dihydrosphingomyelin; and cholesterols, the liposome composition including a drug consisting of topotecan or a salt thereof and having an inner water phase containing ammonium sulfate, and a molar ratio of sulfate ions in the inner water phase to the drug in an entire water phase is 0.36 or more,
    wherein the platinum preparation is not included in the liposome composition.

* * * * *